(12) United States Patent
Lee et al.

(10) Patent No.: US 8,043,789 B2
(45) Date of Patent: *Oct. 25, 2011

(54) PHOTOSENSITIVE COMPOUND AND PHOTORESIST COMPOSITION INCLUDING THE SAME

(75) Inventors: Jae-Woo Lee, Bucheon-Si (KR); Min-Ja Yoo, Boryeong-Si (KR); Jun-Gyeong Lee, Daejeon (KR); Young-Bae Lim, Daegu (KR); Jae-Hyun Kim, Seoul (KR)

(73) Assignee: Dongjin Semichem Co., Ltd., Incheon (KR)

( * ) Notice: Subject to any disclaimer, the term of this patent is extended or adjusted under 35 U.S.C. 154(b) by 194 days.

This patent is subject to a terminal disclaimer.

(21) Appl. No.: 12/337,058

(22) Filed: Dec. 17, 2008

(65) Prior Publication Data

US 2009/0155714 A1 Jun. 18, 2009

(30) Foreign Application Priority Data

Dec. 18, 2007 (KR) .................. 10-2007-0133793

(51) Int. Cl.
*G03F 7/039* (2006.01)
*G03F 7/20* (2006.01)
*G03F 7/30* (2006.01)
*G03F 7/38* (2006.01)

(52) U.S. Cl. ............... 430/270.1; 430/325; 430/326; 430/330; 430/914; 560/55; 560/56; 560/57; 560/59; 560/61; 560/64; 560/73; 560/116; 560/118; 560/119; 560/127; 560/129; 560/130; 560/138; 560/139; 560/140; 560/141; 560/144; 560/146; 560/174; 560/176; 560/190; 560/193; 560/194; 560/198; 560/201; 568/593; 568/633; 568/640; 568/644; 549/415

(58) Field of Classification Search .................. None
See application file for complete search history.

(56) References Cited

U.S. PATENT DOCUMENTS
6,200,729 B1 * 3/2001 Aoai et al. ................. 430/270.1

FOREIGN PATENT DOCUMENTS
JP 2007-119370 * 5/2007

OTHER PUBLICATIONS

Derwent English abstract for JP2007-119370.*
Machine-assisted English translation of JP2007-119370.*

* cited by examiner

*Primary Examiner* — Sin J. Lee
(74) *Attorney, Agent, or Firm* — Birch, Stewart, Kolasch & Birch, LLP

(57) ABSTRACT

A photosensitive compound whose size is smaller than conventional polymer for photoresist, and which has well-defined (uniform) structure, and a photoresist composition including the same are disclosed. The photosensitive compound represented by the following formula. Also, the present invention provides a photoresist composition comprising 1 to 85 wt % (weight %) of the photosensitive compound; 0.05 to 15 weight parts of a photo-acid generator with respect to 100 weight parts of the photosensitive compound; and 10 to 5000 weight parts of an organic solvent.

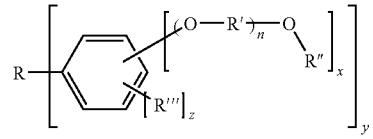

In the formula, n is 0 or 1, x is 1, 2, 3, 4 or 5, y is 2, 3, 4, 5 or 6, z is 0, 1, 2, 3 or 4, R, R' and R" are independently hydrocarbon group of 1 to 30 carbon atoms, preferably 2 to 20 carbon atoms, and R''' is a hydrogen atom or hydrocarbon group of 1 to 30 carbon atoms, preferably 2 to 20 carbon atoms.

7 Claims, 1 Drawing Sheet

[FIG. 1]
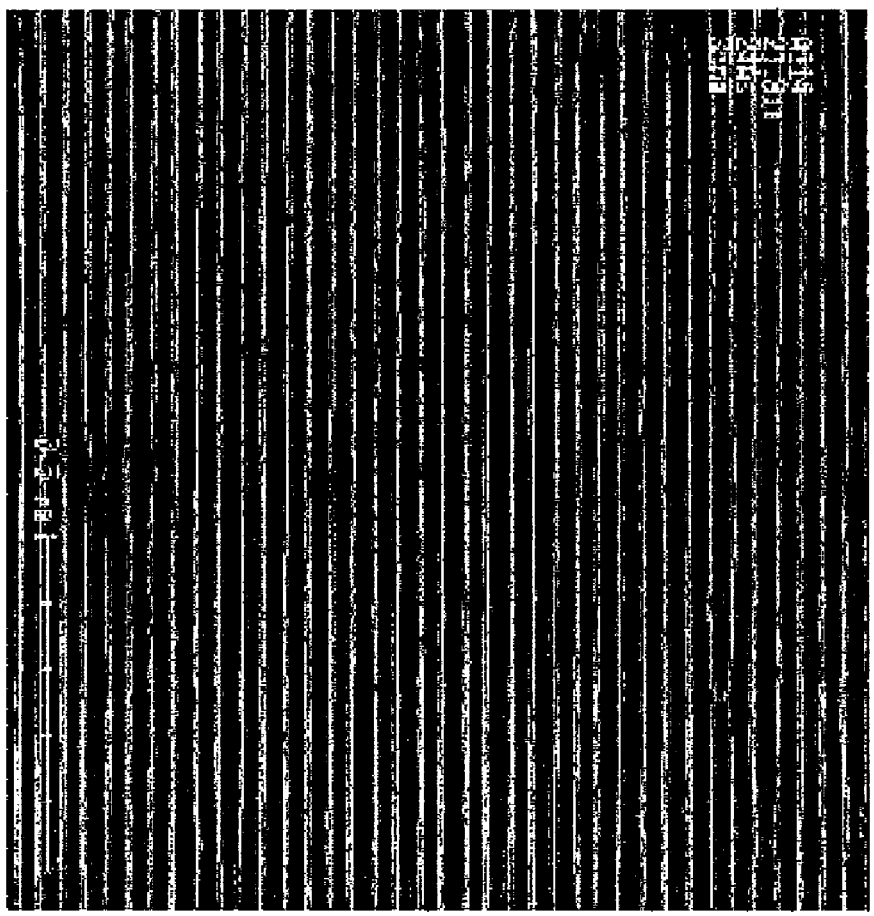

PHOTOSENSITIVE COMPOUND AND PHOTORESIST COMPOSITION INCLUDING THE SAME

This application claims the priority benefit of Korean Patent Application No. 10-2007-0133793 filed on December 18, 2007. All disclosure of the Korean Patent application is incorporated herein by reference.

FIELD OF THE INVENTION

This invention relates to a photosensitive compound and a photoresist composition including the same, and more particularly to a photosensitive compound whose size is smaller than conventional polymer for photoresist and whose structure is well-defined (uniform), and a photoresist composition including the same.

BACKGROUNDS OF THE INVENTION

The photolithography is a process used to form a circuit pattern of a semiconductor chip or a display element from a semiconductor wafer or a glass for the display element. The photoresist composition is the most essential materials to the photolithography process. Recently, as the patterns for semiconductor devices and the display elements are finer, the need for the photoresist composition having high resolution is more increased.

Conventional acid-amplified photoresist composition includes a polymer resin, a photo-acid generator (PAG), an organic solvent and a base compound as occasion demands. Since the conventional photoresist composition includes the polymer resin as a main component, it has excellent mechanical properties such as processibility, coating stability, etching resistance and can be easily removed after the succeeding process including an etching process, an ion implantation process and so on. However, it has disadvantage in that the resolution of photoresist composition is restricted by the size of polymer resin. That is, in the photolithography process, it is impossible to form the pattern which has smaller size than the photosensitive polymer resin included in a photoresist composition. Also, as the structure of semiconductor changes to a fine structure less than 65 nm, the resist which has a polymer as main component do not offer uniformity for fine patterns. This is because the polymer component which is composed of polymer chains of various structures has randomicity to itself.

SUMMARY OF THE INVENTION

Therefore, it is an object of the present invention to provide a photosensitive compound whose size is smaller than conventional polymer for photoresist, and which has well-defined (uniform) structure, and a photoresist composition including the same.

It is another object of the present invention to provide a photosensitive compound which can improve resolution of lithography process, and has an advanced line edge roughness (LER), and can improve uniformity of layer after coating or forming pattern, and a photoresist composition including the same.

It is still another object of the present invention to provide a photosensitive compound which has excellent dry etch resistance, and can reduce the formation of a scum, and a photoresist composition including the same.

In order to achieve these objects, the present invention provides a photosensitive compound having a structure selected from a group consisting of following Formula 1a and following Formula 1b.

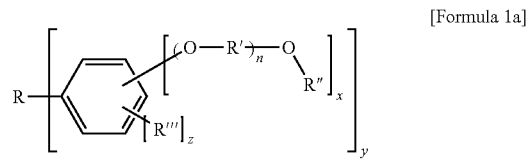

[Formula 1a]

In the Formula 1a, n is 0 or 1, x is 1, 2, 3, 4 or S, y is 2, 3, 4, 5 or 6, z is 0, 1, 2, 3 or 4. R, R' and R" are independently hydrocarbon group of 1 to 30 carbon atoms, preferably 2 to 20 carbon atoms, and R'" is a hydrogen atom or hydrocarbon group of 1 to 30 carbon atoms, preferably 2 to 20 carbon atoms.

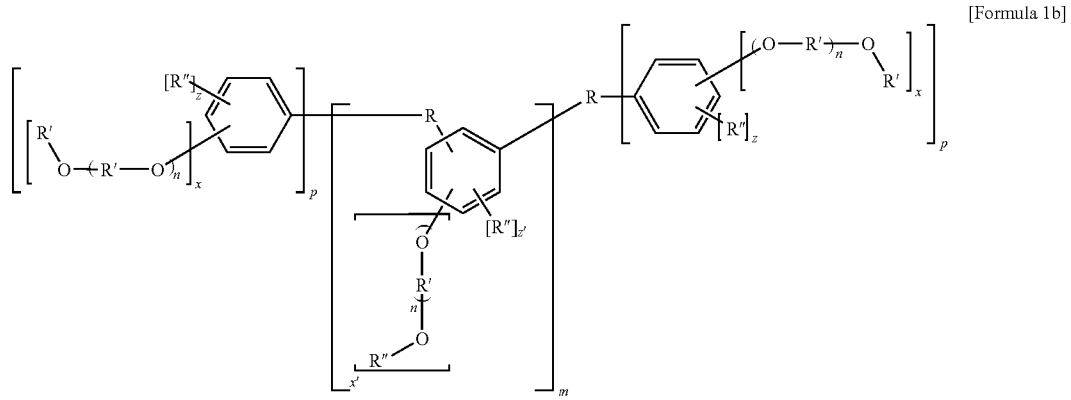

[Formula 1b]

In the Formula 1b, n, x, z, R, R' R" and R'" are the same defined as in Formula 1a. x' is 1, 2, 3 or 4, z' is 0, 1, 2 or 3, and p and m are independently 1 or 2.

The present invention also provides a photoresist composition comprising 1 to 85 wt % (weight %) of the photosensitive compound; 0.05 to 15 weight parts of a photo-acid generator with respect to 100 weight parts of the photosensitive compound; and a remaining organic solvent. The present invention also provides a method for forming photoresist pattern composition comprising the step of: (a) coating a photoresist composition on a substrate to form a photoresist layer; (b) exposing the photoresist layer to a light; (c) heating the exposed photoresist layer; and (d) developing the heated photoresist layer to form the photoresist pattern.

In the photoresist composition of the present invention, the resolution of the photoresist is enhanced by minimizing the dimension of constructing unit of the photosensitive layer so that the minimum resolution of the lithography process can be improved less than 32 nm. Also, a constructing unit for forming the photoresist pattern is small sized and is of simple pure material so that semi-conductive property can be insured by controlling LER less than 3 mm. The attraction between constructing units is uniform so that the coating uniformity can remain within 3%. Besides, in the photoresist composition according to the present invention, the amount of benzene rings in the molecule composing the photosensitive layer is much so that dry etching resistance is enhanced similarly to novolac resin and the generation of abnormal pattern after development, that is scum, can be inhibited sufficiently. The scum is caused by components insoluble to the developer and causes uneven etching.

BRIEF DESCRIPTION OF THE DRAWINGS

FIG. 1 shows an electron microphotograph of the photoresist pattern formed by using a photoresist composition according to one embodiment of the present invention

DETAILED DESCRIPTION OF THE INVENTION

A more complete appreciation of the invention, and many of the attendant advantages thereof, will be better appreciated by reference to the following detailed description.

The photosensitive compound according to the present invention has a structure which can be deprotected by an acid, and is represented by the following Formula 1a.

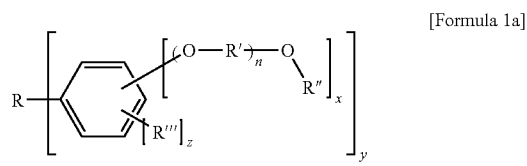

[Formula 1a]

In Formula 1a, n is 0 or 1, x is 1, 2, 3, 4 or 5, y is 2, 3, 4, 5 or 6, z is 0, 1, 2, 3 or 4. R, R' and R" are independently hydrocarbon group of 1 to 30 carbon atoms, preferably 2 to 20 carbon atoms, and R'" is a hydrogen atom or hydrocarbon group of 1 to 30 carbon atoms, preferably 2 to 20 carbon atoms. The R, R', R" and R'" may be a chain type and/or a ring type of aliphatic and/or aromatic hydrocarbon group, and if necessary, can comprise a substituent such as a carbonyl group, a phenyl group, a sulfonyl group, a fluoroalkyl group, hydroxyl group or 1 to 8 hetero-atoms. For example, carbonyl (C=O) groups or carboxyl (—COO—) groups are positioned at the both ends of the R and R', and the R" can include an ether compound or an ester compound structure which includes oxygen (O) atom.

The representative examples of the photosensitive compound represented by the Formula 1a are as follows.

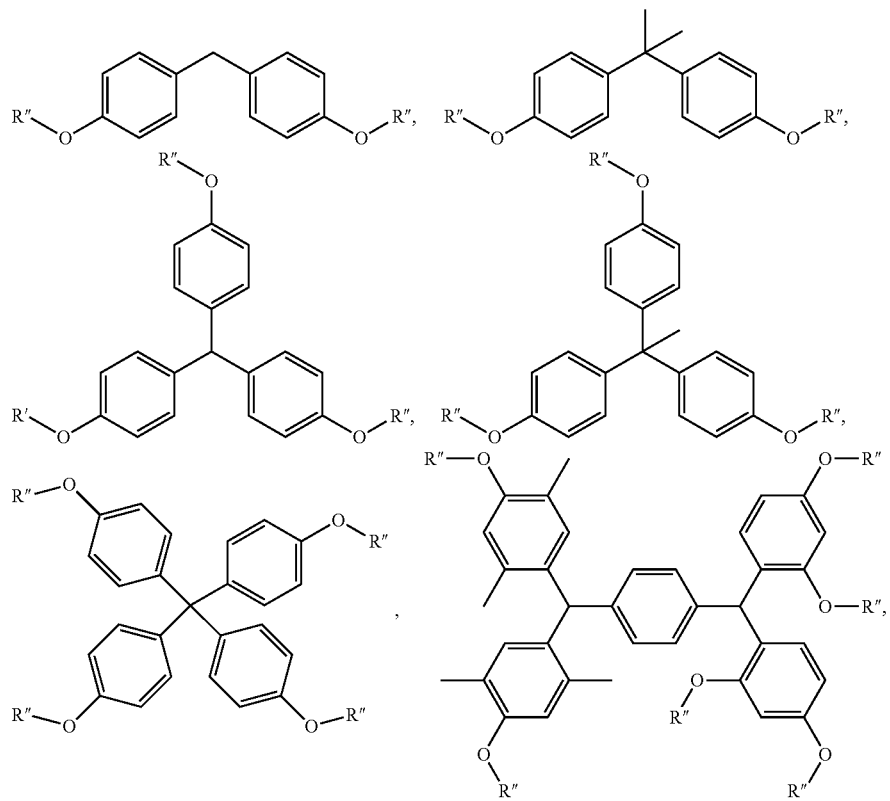

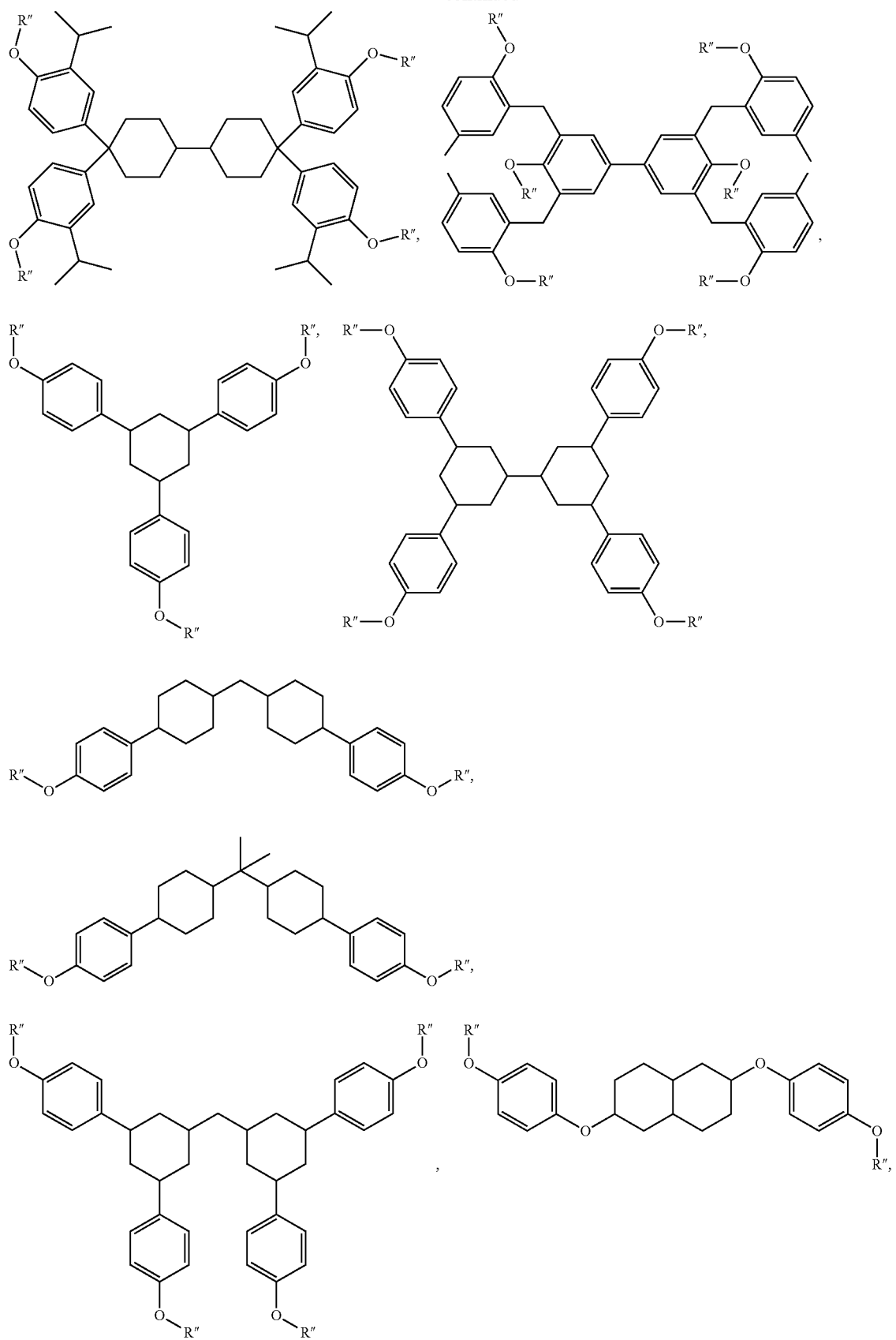

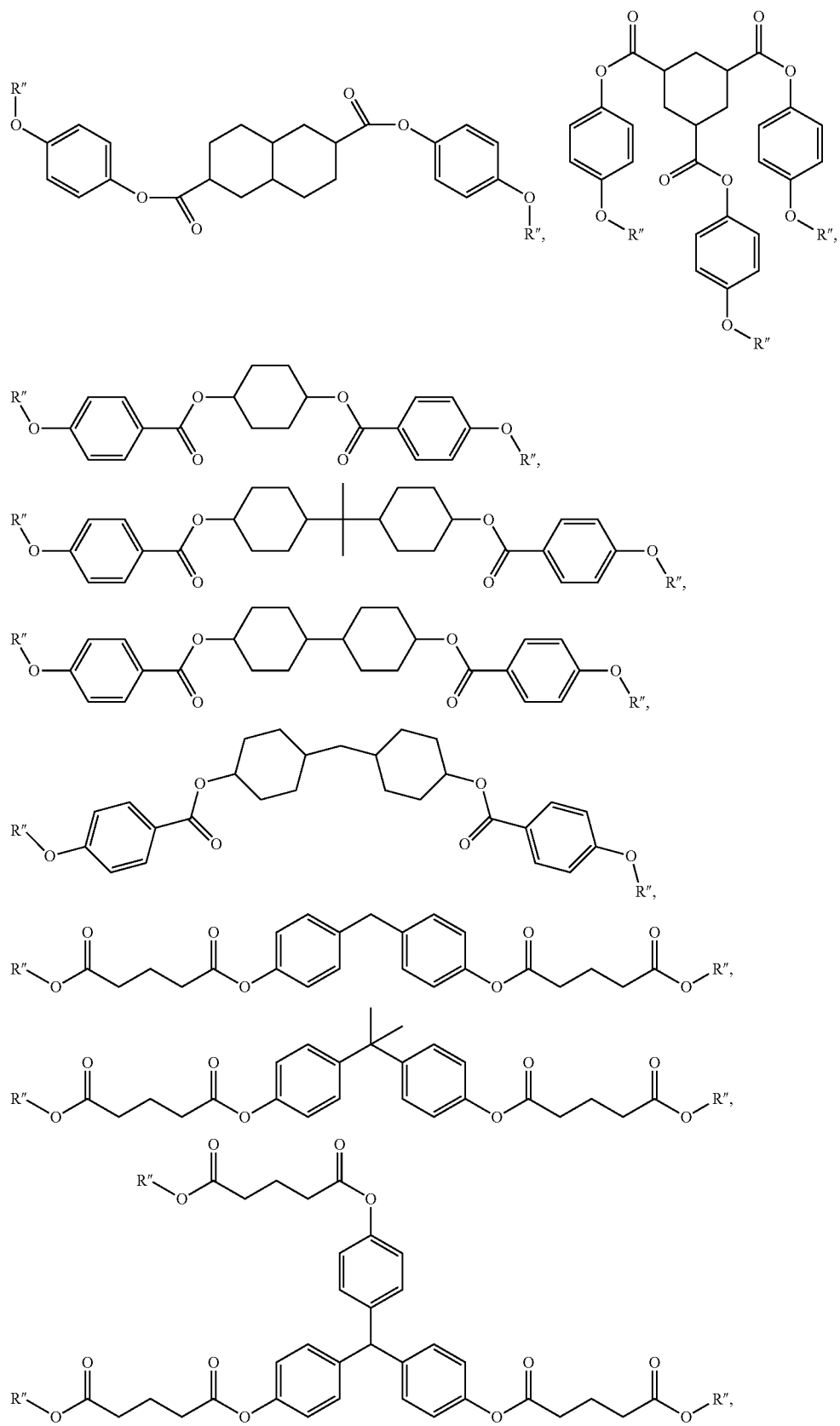

-continued
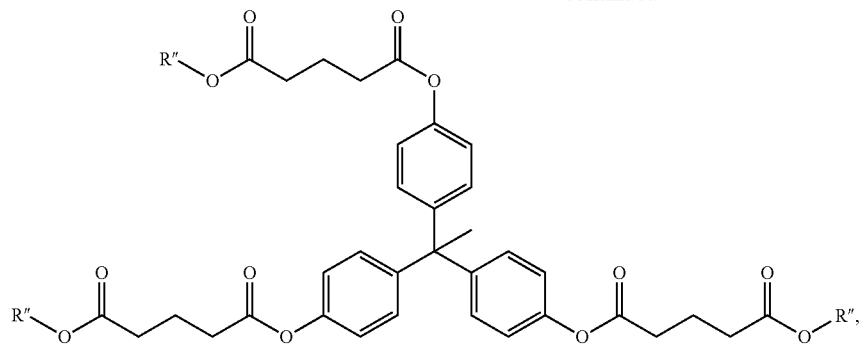
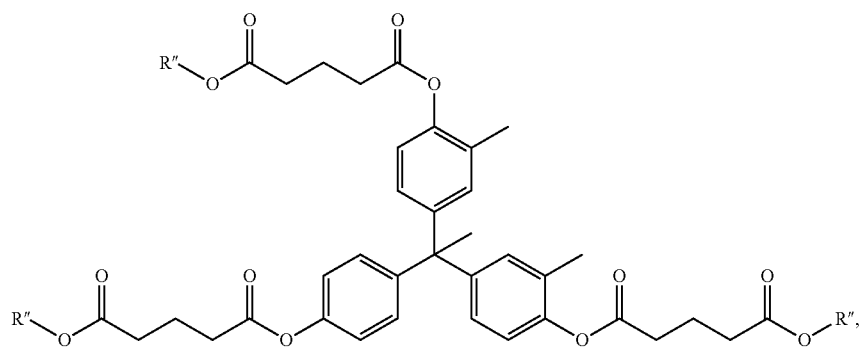
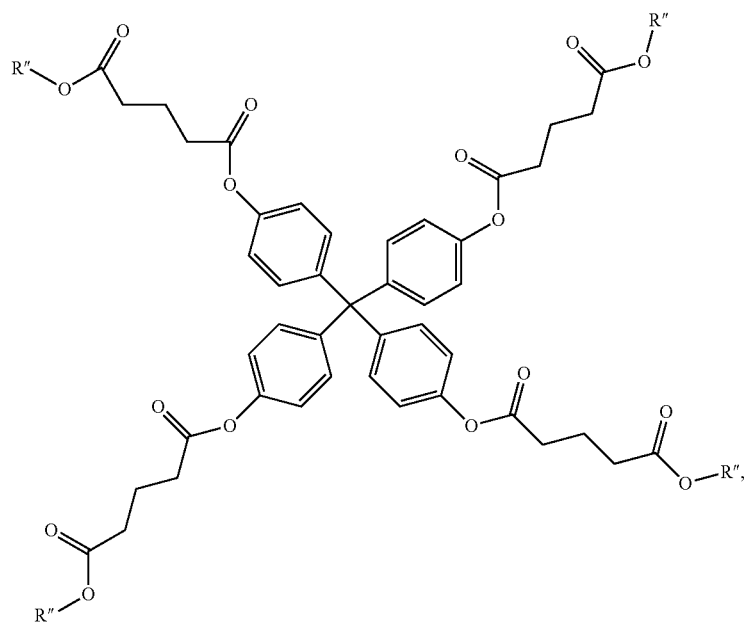

-continued
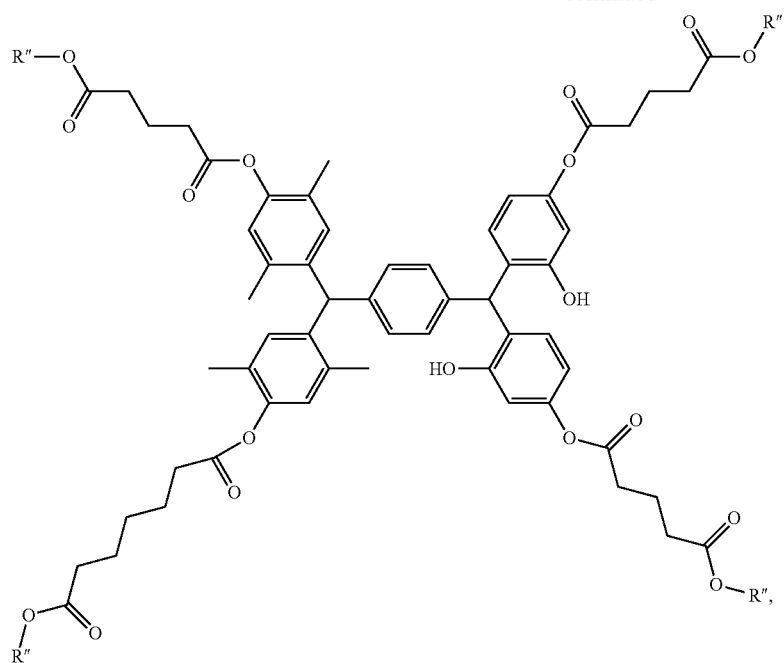
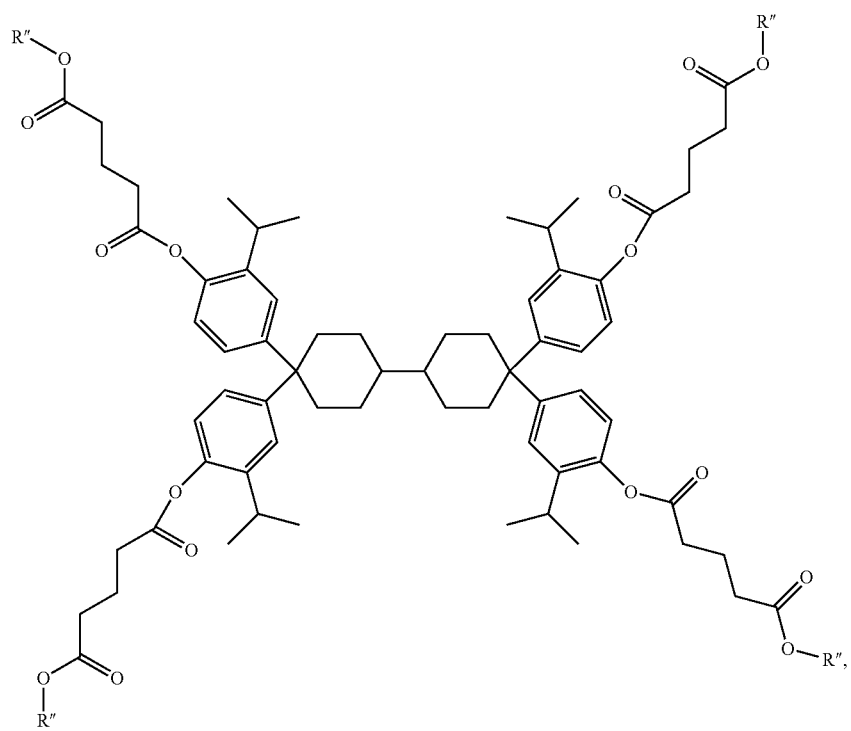

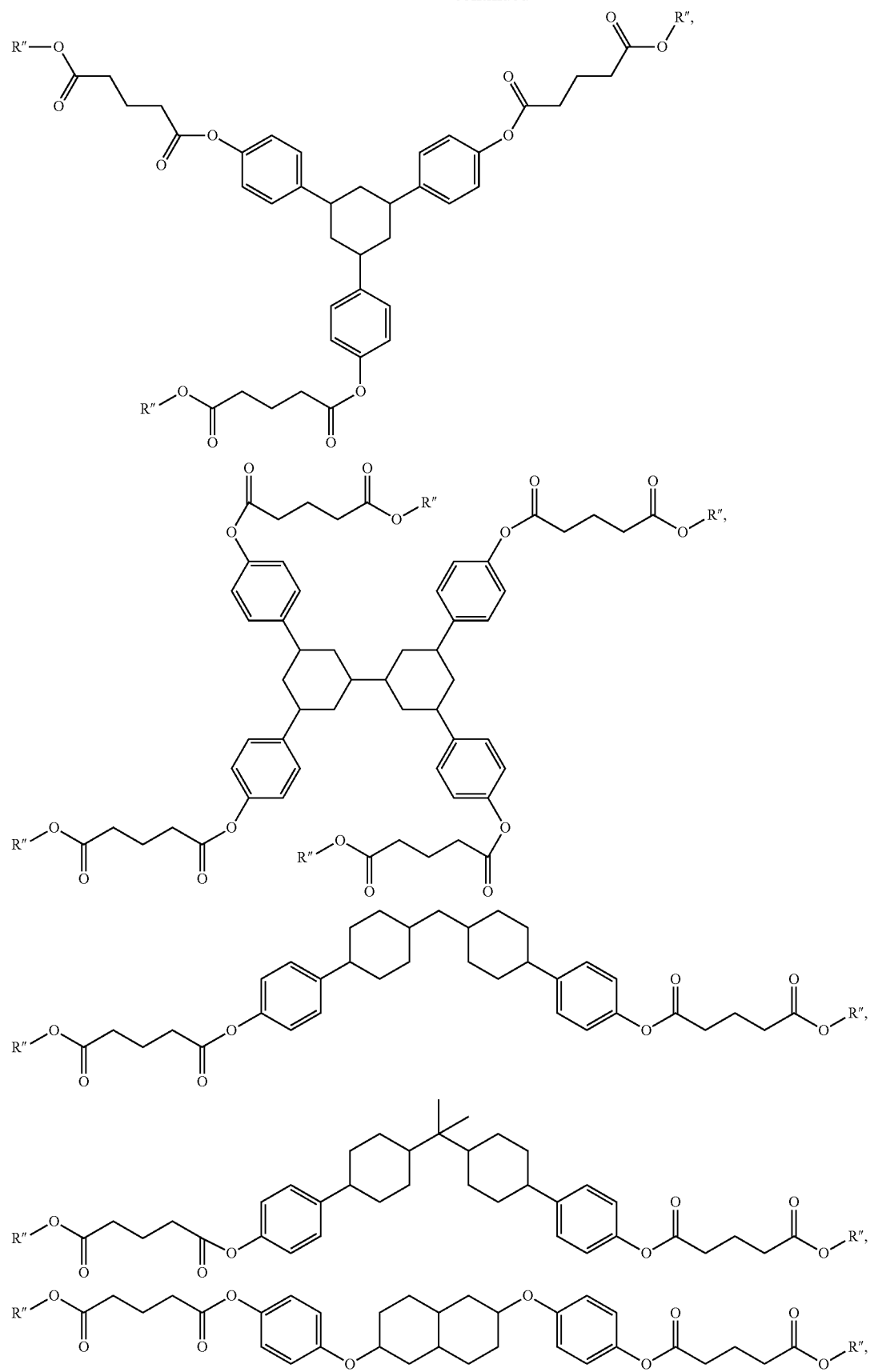

-continued
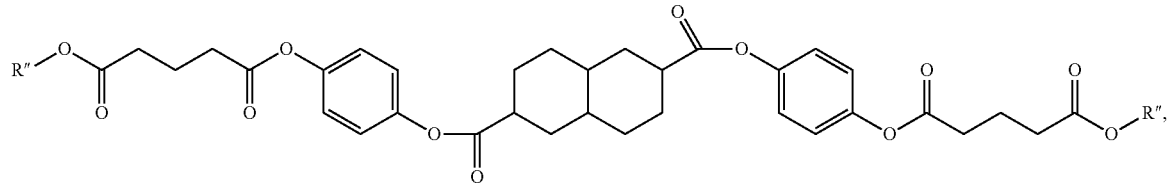
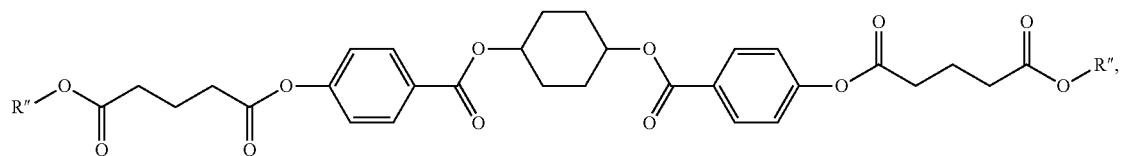
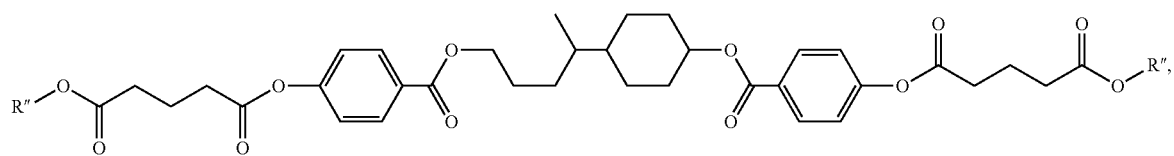
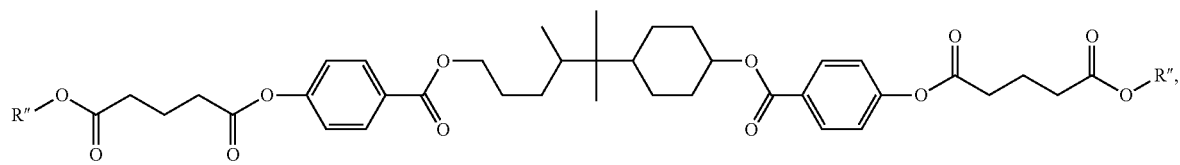
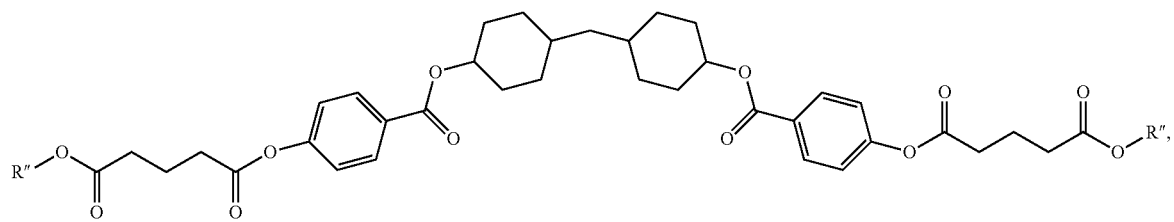
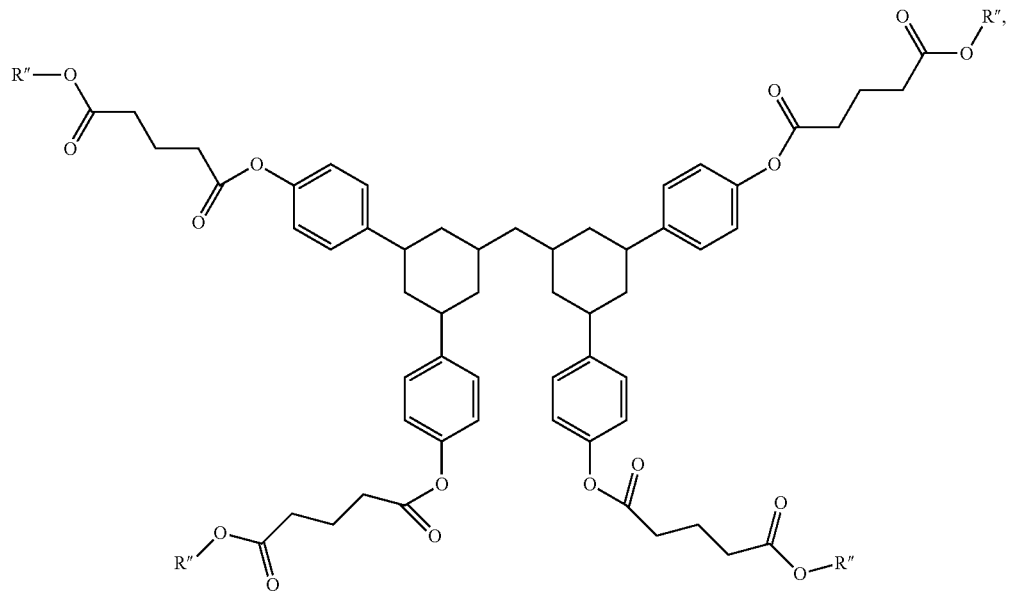

-continued
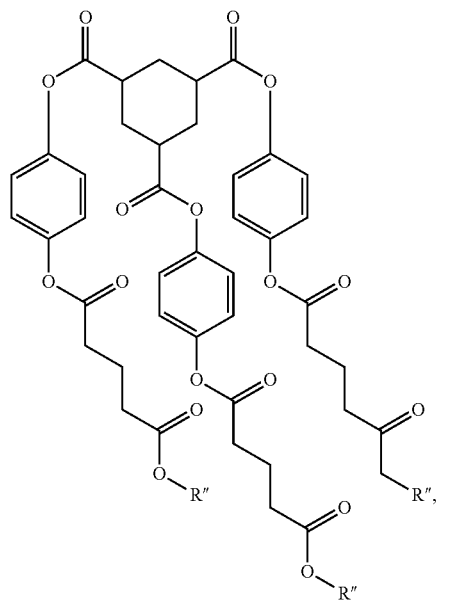
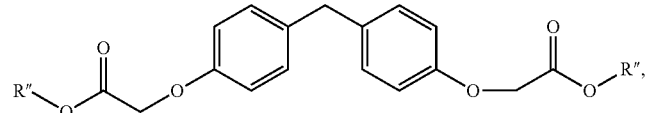
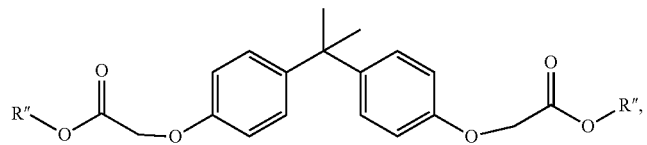
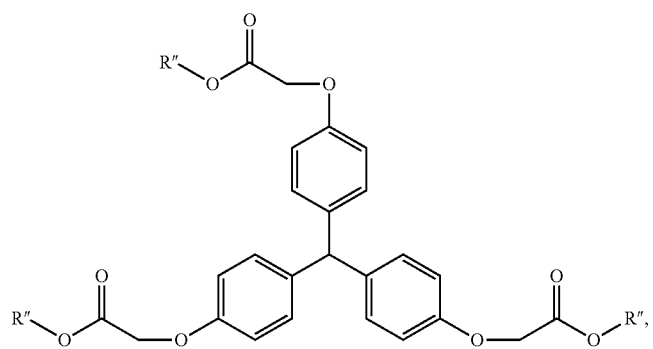
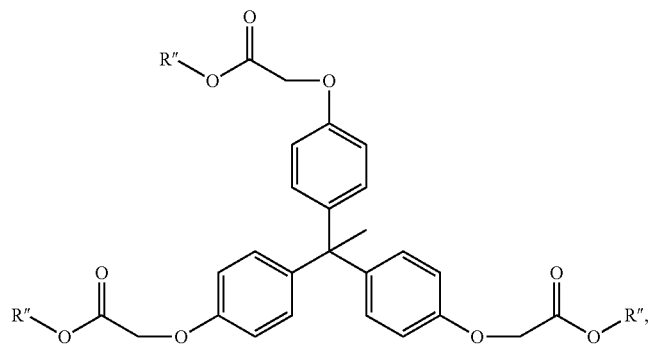

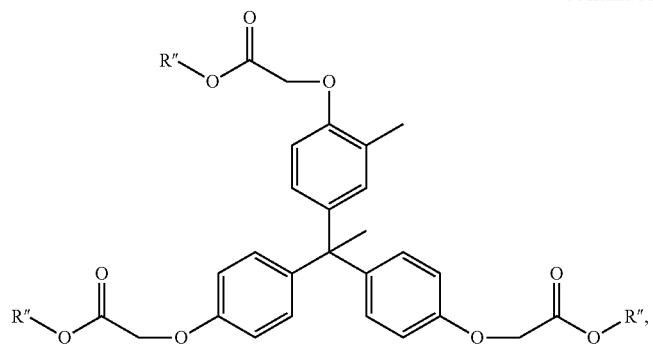
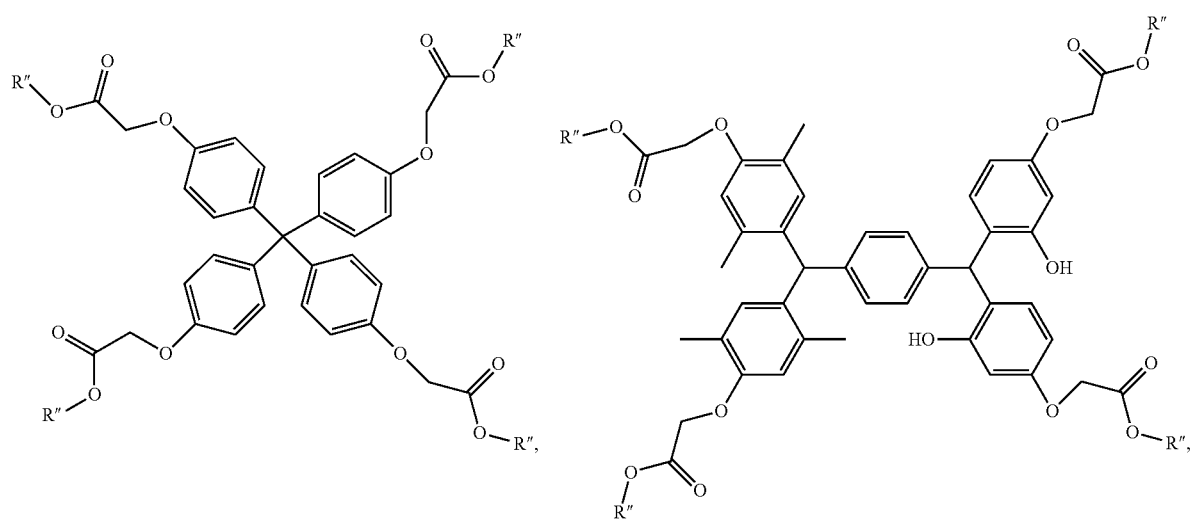
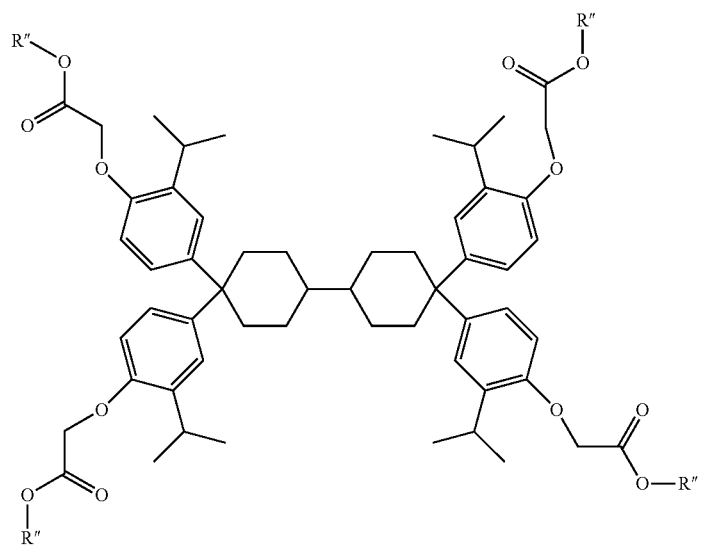

-continued
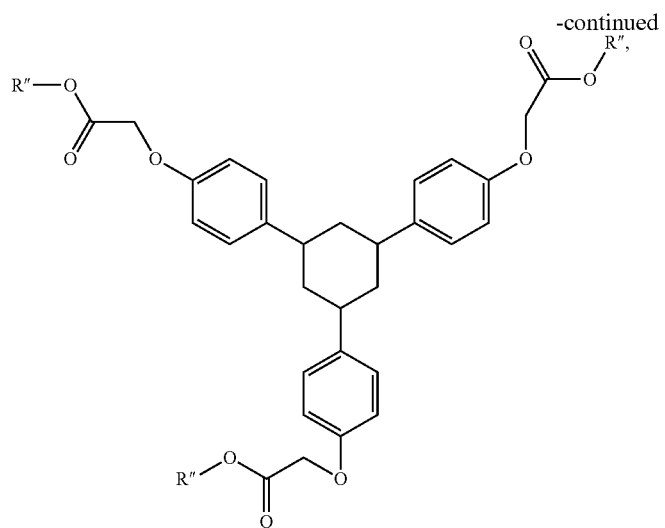
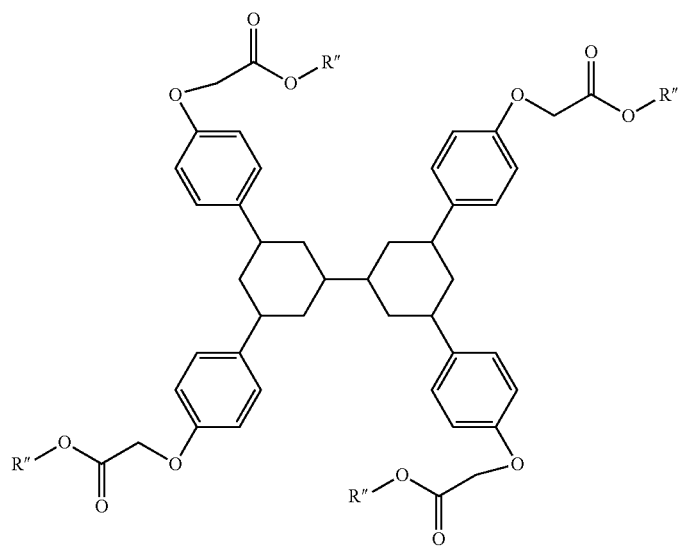
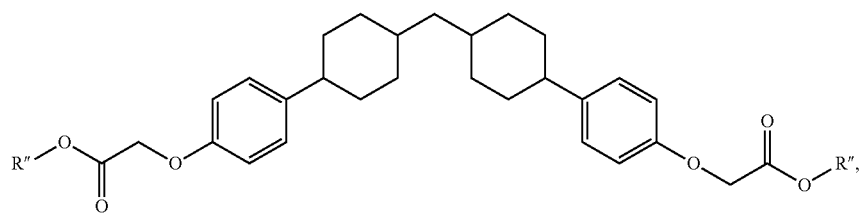
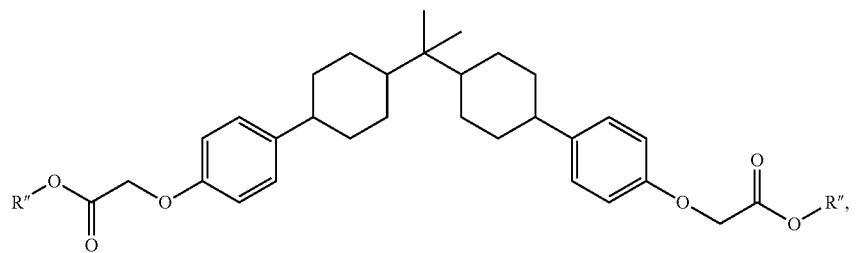

-continued
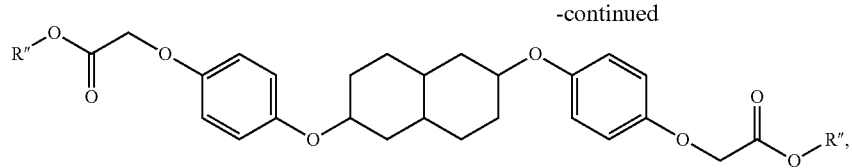
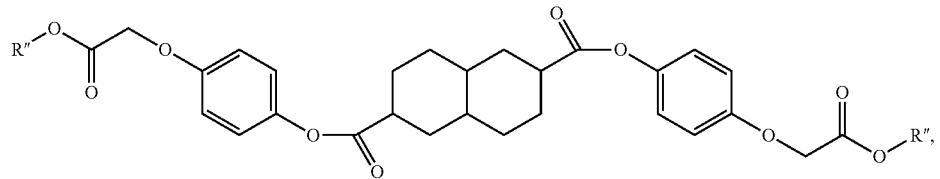
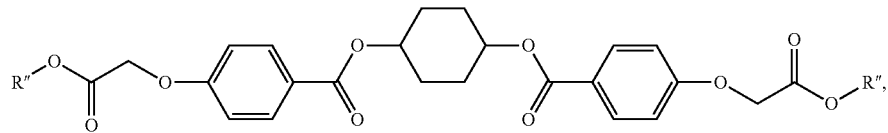
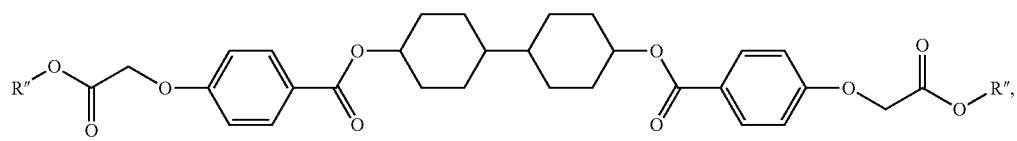
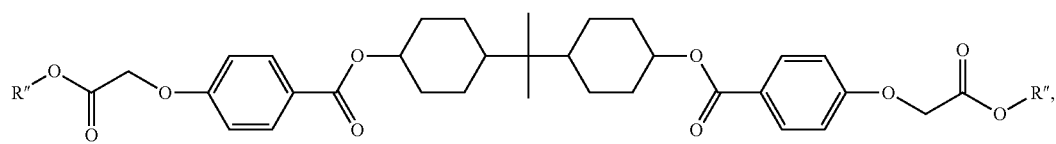
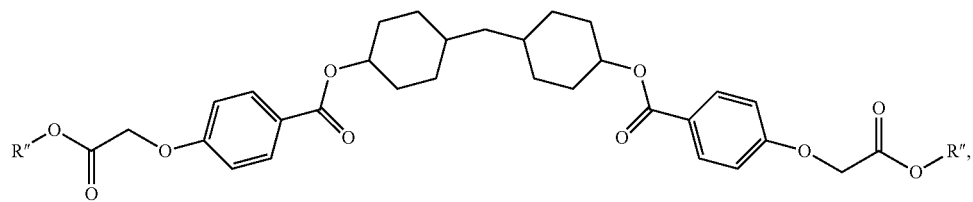
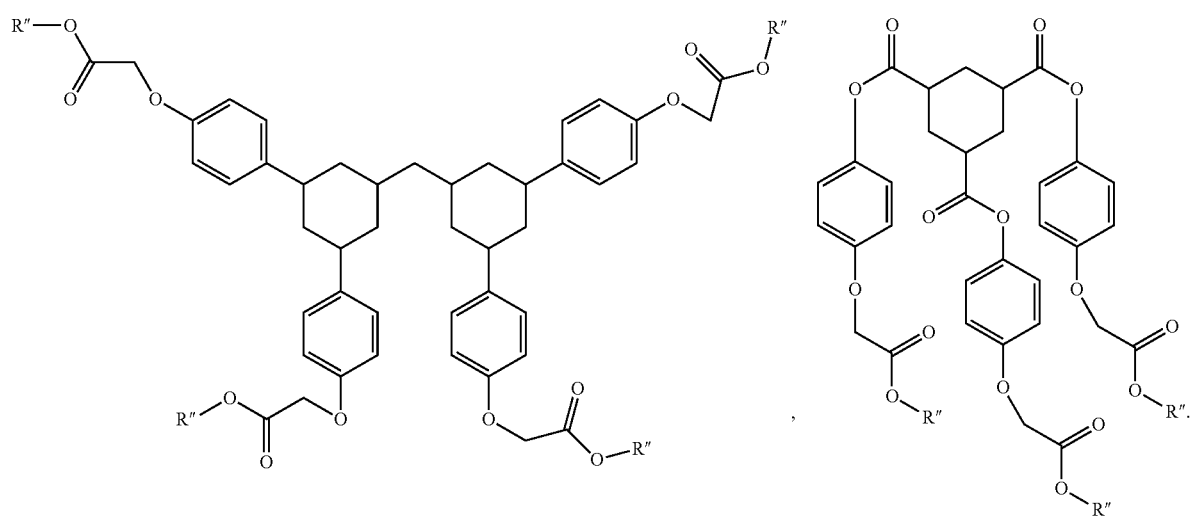

Also, the present invention provides a photosensitive compound represented by the following Formula 1b.
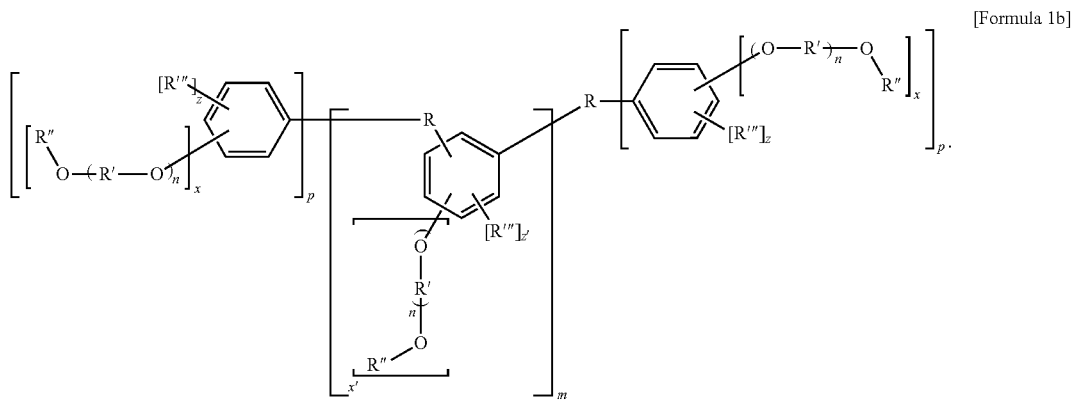
[Formula 1b]
In Formula 1b, n, x, z, R, R'R" and R'" are the same defined as in Formula 1a. x' is 1, 2, 3 or 4, z' is 0, 1, 2 or 3, and p and m are independently 1 or 2.
The representative examples of the photosensitive compound represented by the Formula 1b are as follows.
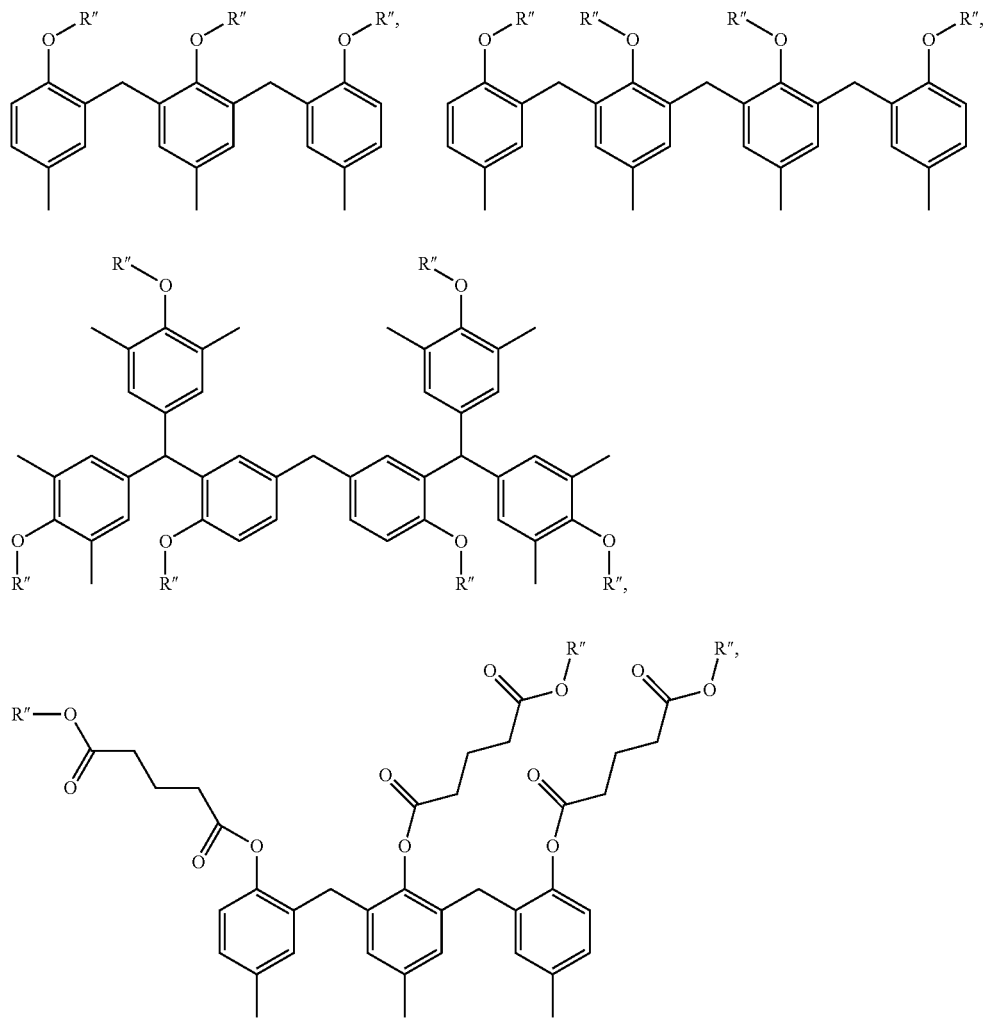

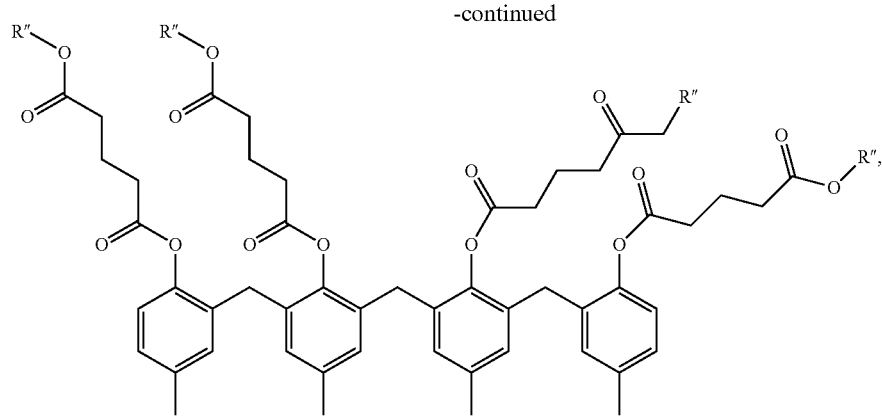
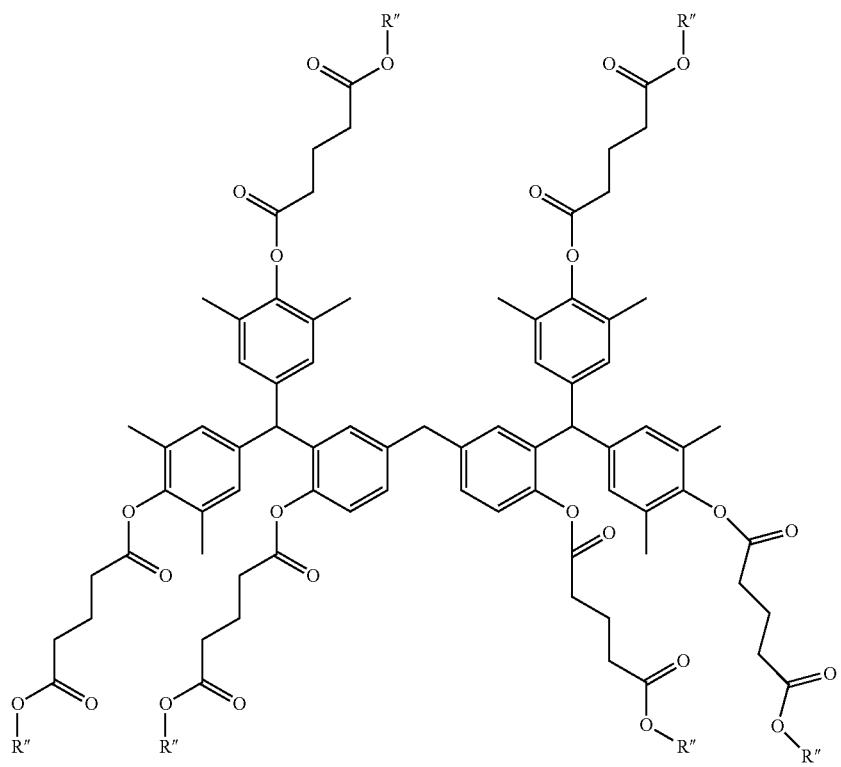
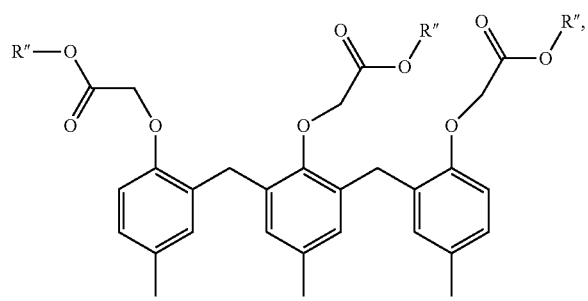

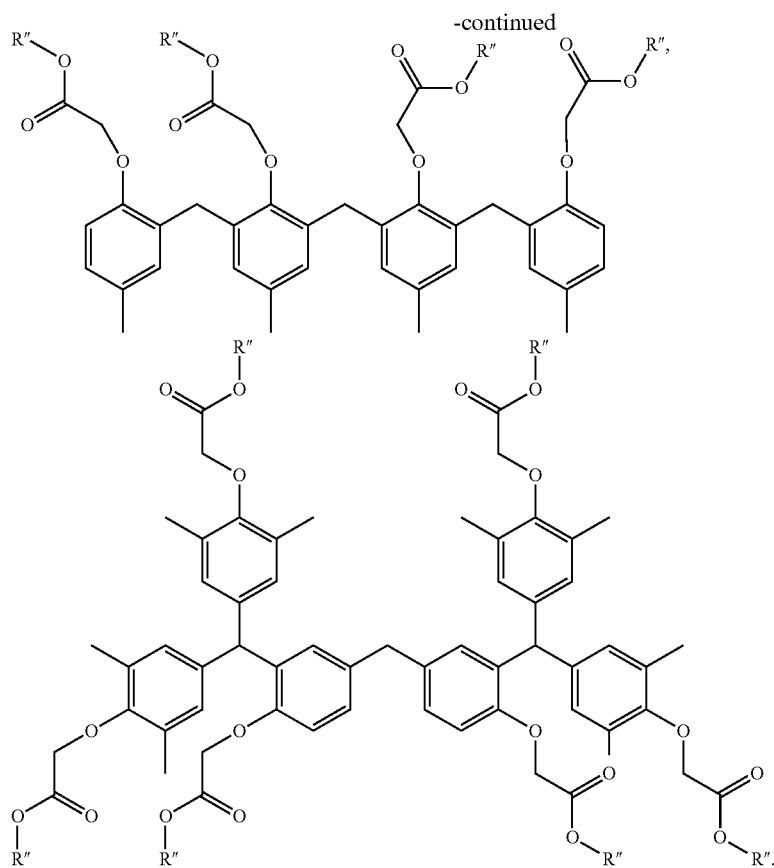
In the Formulas, R" is the same as defined in Formula 1a, and for example has the following structures (wherein, the broken line indicates a bonding part).
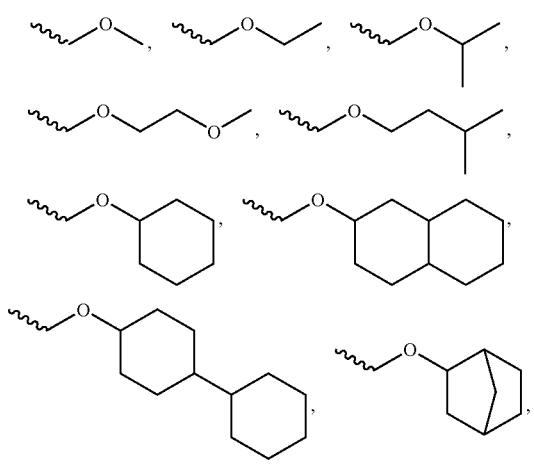
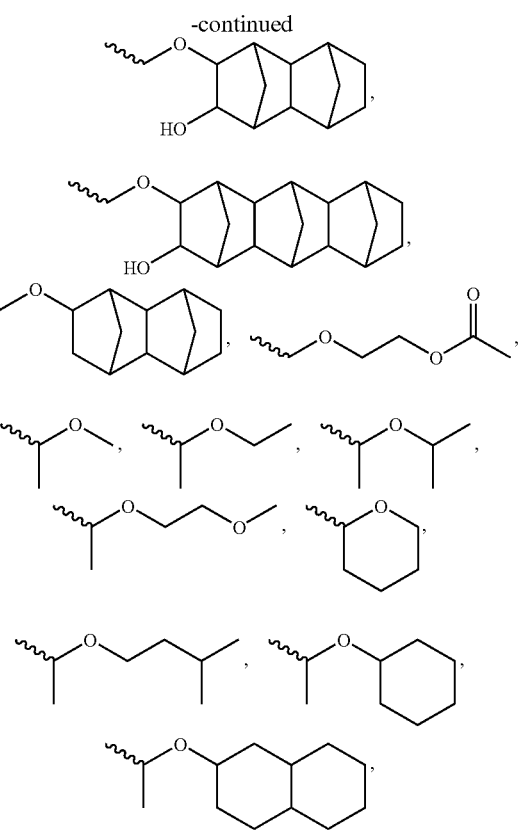

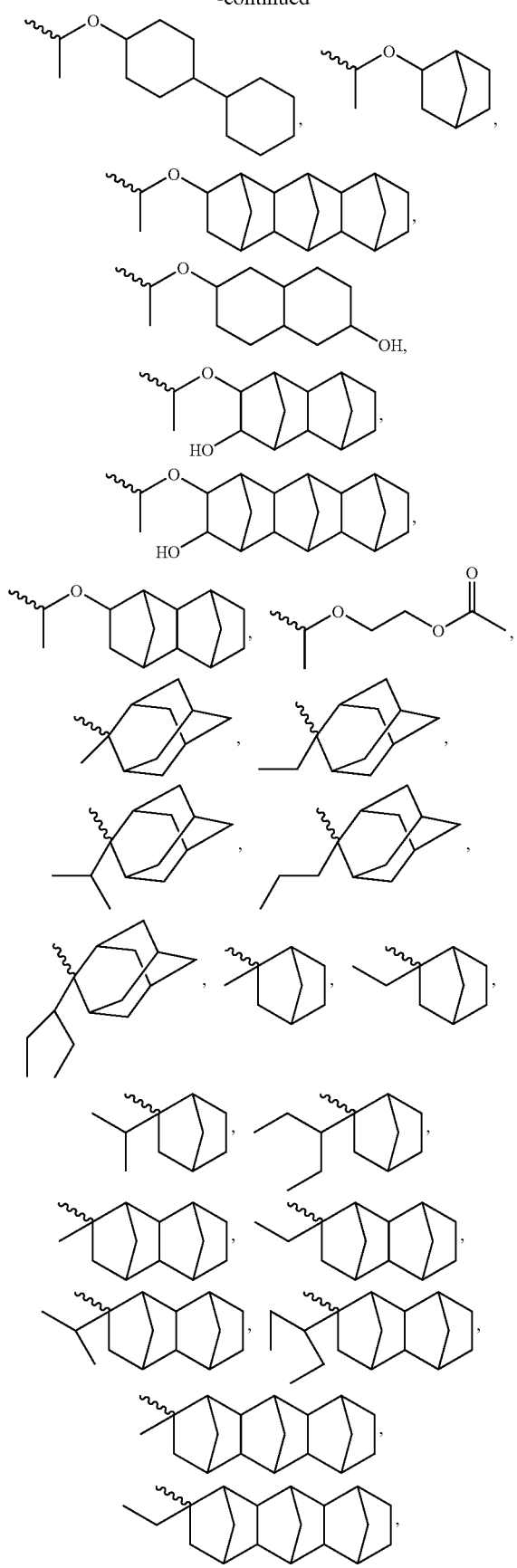
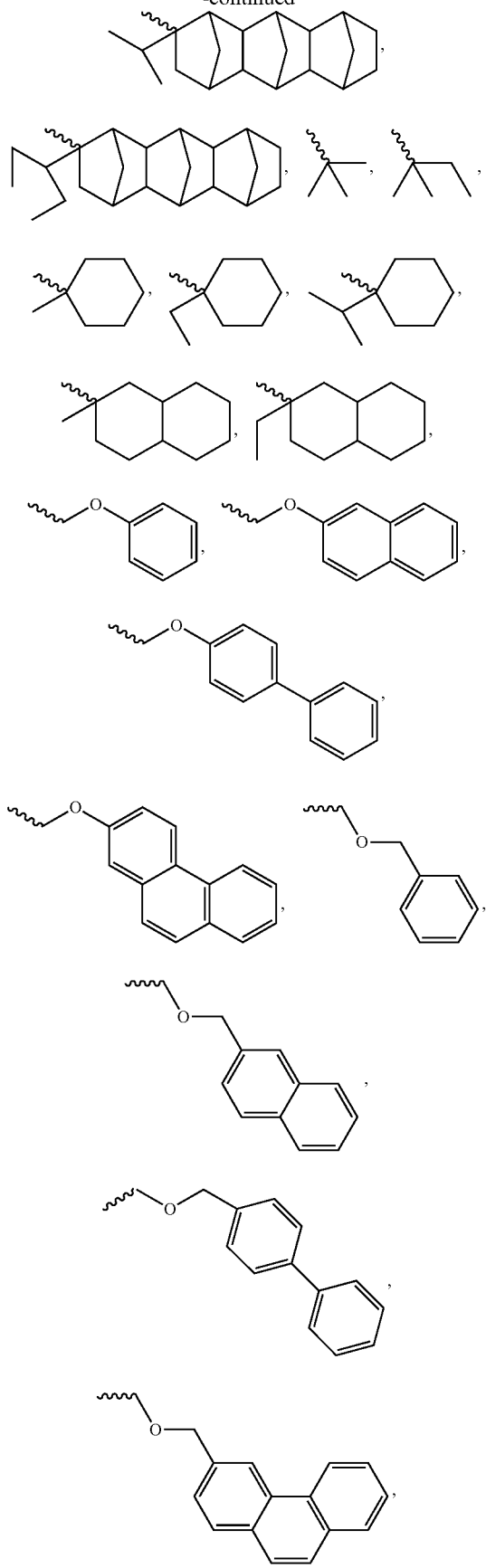

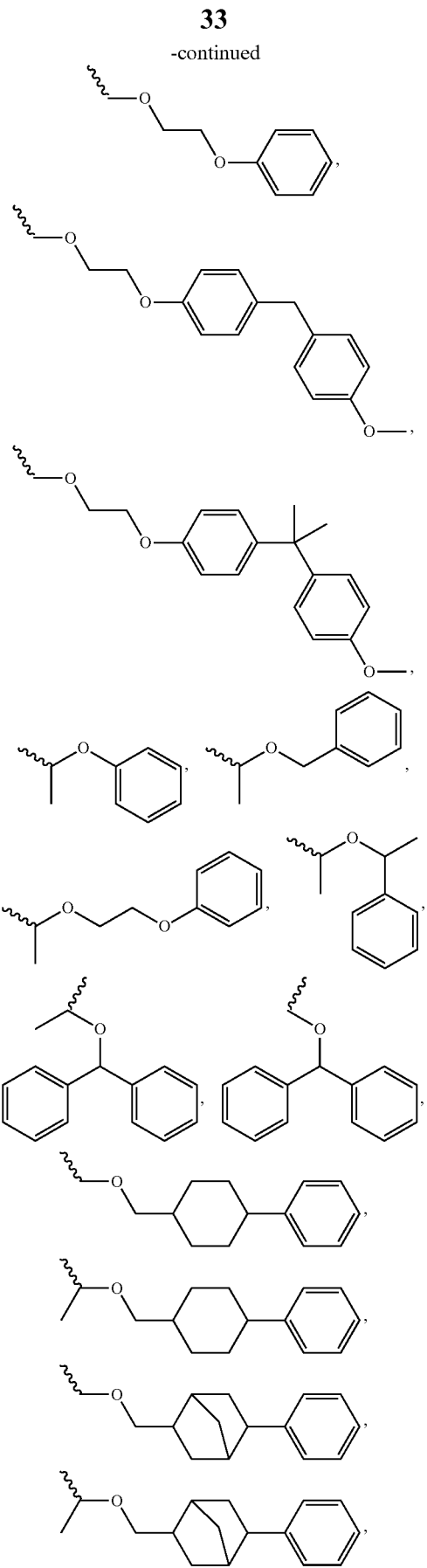

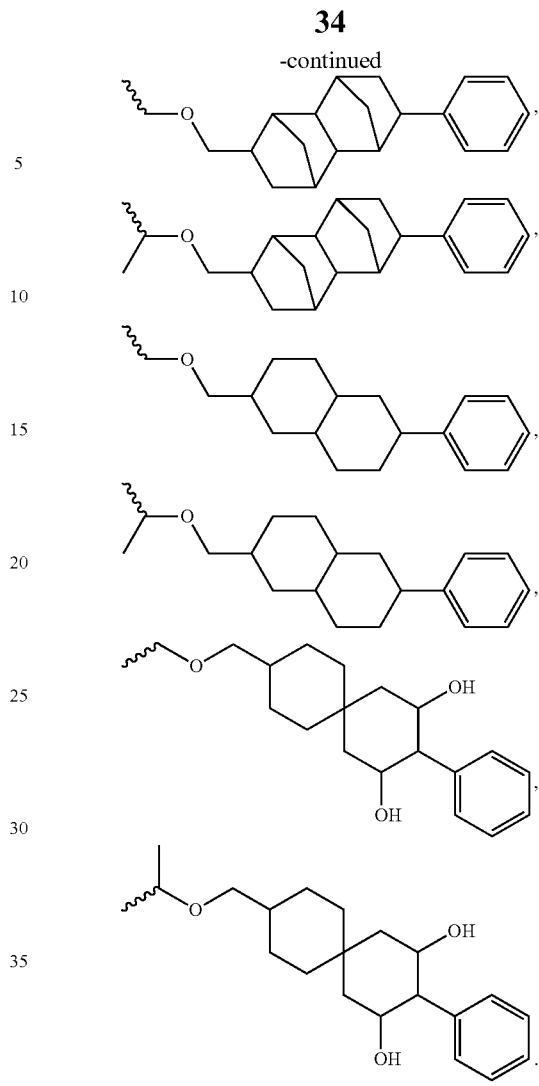

The photosensitive compound according to the present invention has more well-defined (uniform) structure because the photosensitive compound has a smaller size than a conventional polymer for photoresist, and has a uniform size and structure. Besides, the acid formed by photo-acid generator under exposing process, deprotects the dissolution inhibitor protecting group so that the solubility in developer is increased to selectively develop only the exposed region.

The photosensitive compound of the present invention can be synthesized by conventional organic synthesis methods. For example, the photosensitive compound is synthesized by attaching R" to the hydroxyl group which is substituted at the phenyl group as described in the following Reaction 1 (in case where n is 0 in Formula 1a), by introducing

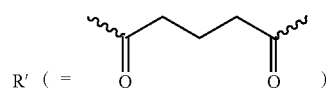

to the hydroxyl group which is substituted at the phenyl group and then again combining R" as described in the following Reaction 2 (in case where n is 1 in Formula 1a), or by simultaneously introducing

and R″ to the hydroxyl group which is substituted at the phenyl group as described in the following Reaction 3 (in case where n is 1 in Formula 1a).

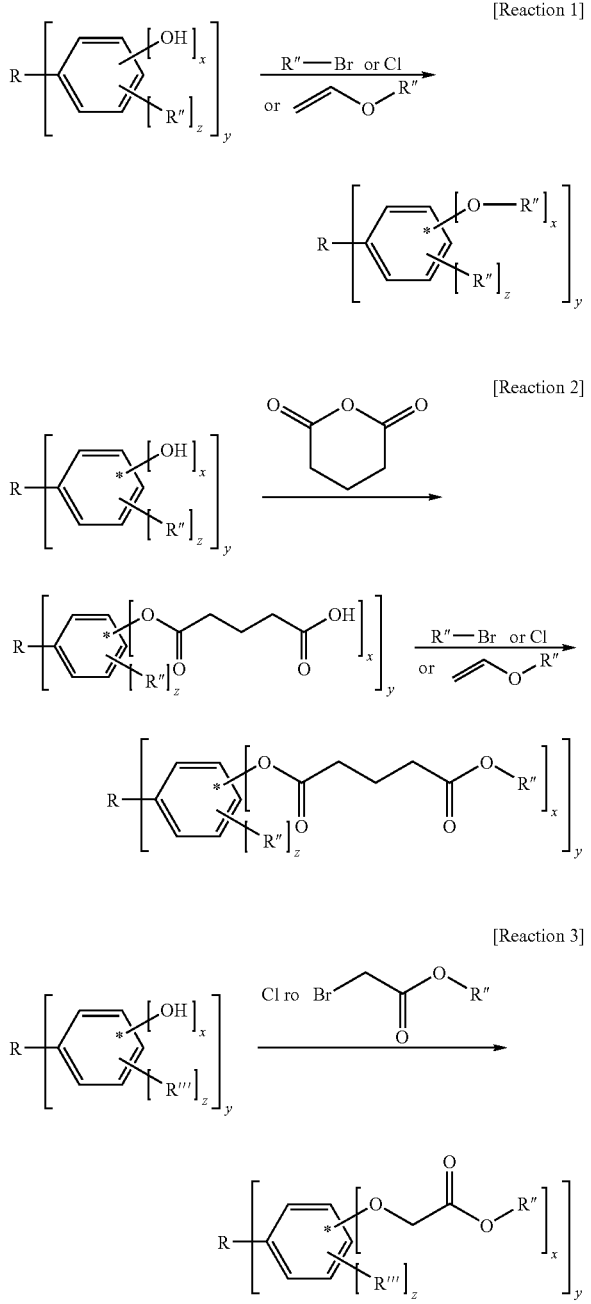

In Reaction 1 to Reaction 3, n, x, y, R, R″ and R‴ are the same as defined in Formula 1a.

The photoresist composition according to the present invention includes the photosensitive compound represented by the Formula 1a or Formula 1b, a photo-acid generator and an organic solvent, and, if necessary, further includes a base compound as a quencher, and a surfactant. In the photoresist composition, the amount of the photosensitive compound is 1 to 85 wt % (weight %), preferably 10 to 45 wt %, more preferably 10 to 25 wt %. The amount of the photo-acid generator is 0.05 to 15 weight parts, preferably 0.15 to 10 weight parts, further preferably 1 to 5.5 weight parts with respect to 100 weight parts of the photosensitive compound. The amount of the organic solvent is 10 to 5000 weight parts, preferably 200 to 5000 weight parts, further preferably 250 to 4000 weight parts with respect to 100 weight parts of the photosensitive compound. Also, the amount of the base compound, if used, is 0.01 to 10 weight parts, preferably 1 to 2 weight parts with respect to 100 weight parts of the photosensitive compound. If the amount of the photosensitive compound is too little (less than 1 wt %), it is difficult to form the photoresist layer with a desired thickness. If the amount of the photosensitive compound is too much (more than 85 wt %), the thickness of patterns formed on the wafer may be not uniform. Also, if the amount of the PAG (photo-acid generator) is too little (less than 0.05 weight parts), the light sensitivity of the photoresist composition may decrease. If the amount of the PAG is too much (more than 15 weight parts), the profile of the photoresist patterns may be deteriorated because the PAG absorbs a lot of ultraviolet rays and a large quantity of acid is produced from the PAG. Also, if the amount of the base compound is too little (less than 0.01 weight parts), it is not easy to control a diffusion of the acid generated in an exposure process so that the pattern profile is uneven. If the amount of the base compound is too much (more than 10 weight parts), the diffusion of the acid generated is suppressed so that pattern is not easily formed.

As the PAG (photo-acid generator), any conventional PAG which can generate an acid when exposed to a light, can be used. The non-limiting examples of the PAG include onium salts such as sulfonium salts or iodonium salts. Specifically, the PAG is selected from a group consisting of phthalimidotrifluoromethane sulfonate, dinitrobenzyltosylate, n-decyl disulfone and naphthylimido trifluoromethane sulfonate. Also, the PAG is selected from the group consisting of diphenyl iodonium triflate, diphenyl iodonium nonaflate, diphenyl iodonium hexafluorophosphate, diphenyl iodonium hexafluoroarsenate, diphenyl iodonium hexafluoroantimonate, diphenyl p-methoxyphenyl sulfonium triflate, diphenyl p-toluenyl sulfonium triflate, diphenyl p-tert-butylphenyl sulfonium triflate, diphenyl p-isobutylphenyl sulfonium triflate, triphenylsulfonium triflate, tris(p-tert-butylphenyl) sulfonium triflate, diphenyl p-methoxyphenyl sulfonium nonaflate, diphenyl p-toluenyl sulfonium nonaflate, diphenyl p-tert-butylphenyl sulfonium nonaflate, diphenyl p-isobutylphenyl sulfonium nonaflate, triphenylsulfonium nonaflate, tris(p-tert-butylphenyl) sulfonium nonaflate, triphenylsulfonium hexafluoroarsenate, triphenylsulfonium hexafluoroantimonate, triphenylsulfonium triflate and dibutylnaphtylsulfonium triflate.

As the organic solvent, the conventional various organic solvents for the photoresist composition can be used. Exemplary organic solvents include, but are not limited to, ethyleneglycol monomethylethyl, ethyleneglycol monoethylether, ethyleneglycol monomethylether, ethyleneglycol monoacetate, diethylene glycol, diethyleneglycol monoethylether, propyleneglycol monomethyletheracetate (PGMEA), propyleneglycol, propyleneglycol monoacetate, toluene, xylene, methylethylketone, methyl isoamyl ketone, cyclohexanone, dioxane, methyl lactate, ethyl lactate, methyl pyruvate, ethyl pyruvate, methyl methoxy propionate, ethyl ethoxy propionate, N,N-dimethylformamide, N,N-dimethylacetamide, N-methyl-2-pyrollidone, 3-ethoxy ethyl propionate, 2-heptanone, gamma-butyrolactone, ethyl 2-hydroxy propionate, ethyl 2-hydroxy-2-methyl propionate, ethoxyethyl acetate, hydroxylethyl acetate, methyl 2-hydroxy-3-methylbutanoate, methyl 3-methoxy-2-methylpropionate, ethyl 3-ethoxy propionate, ethyl 3-methoxy-2-methyl propionate, ethyl acetate, butyl acetate, and mixture thereof.

Also, as the base compound which is used as quencher or reaction inhibitor, the conventional quenchers or reaction inhibitors, for example, organic bases such as tri-ethylamine, trioctylamine, tri-iso-butylamine, tri-iso-octylamine, di-ethanolamine, tri-ethanolamine and mixture thereof, can be used without limitation. The surfactant, at need, is added in the present photoresist composition so as to improve a mixing uniformity of the photoresist composition, coating property of the photoresist composition and developing property of the photoresist film after the light exposure. As the surfactant, conventional various surfactant used in the photoresist composition can be used. Exemplary surfactants include, but are not limited to, fluorine-based surfactant or fluorine-silicon-based surfactant. The amount of the surfactant is 0.001 to 2 weight parts, preferably 0.01 to 1 weight parts with respect to solid content 100 weight parts of the photoresist composition. If the amount of the surfactant is too little, function of surfactant does not sufficiently work, and if the amount of the surfactant is too much, the resist property such as shape stability or a storage stability of the composition except for the coating property, may be adversely affected. Also, if necessary, the photosensitive polymer according to the present invention further comprises a conventional photosensitive polymer for the photoresist which reacts with an acid and whose solubility to a developer is changed, within the limits not to interfere the role of the light sensitive compound of the present invention. The photosensitive polymer may be block copolymer or random copolymer having acid sensitive protecting group, and the weight average molecular weight (Mw) of photosensitive polymer is preferably 3,000 to 20,000.

In order to form a photoresist pattern with the photoresist composition according to the present invention, the following conventional photolithography process can be carried out. First, the photoresist is applied or coated on a substrate such as silicon wafer, an aluminum substrate, and so on, for example, with a spin coater to form a photoresist layer. The photoresist layer is exposed to a light of a predetermined pattern. After the exposure, if necessary, the photoresist pattern is thermally treated (heated), which is called as PEB (Post Exposure Bake), and is developed to form the photoresist pattern. As the developing solution for the developing process, an alkali aqueous solution including an alkali compound such as sodium hydroxide, potassium hydroxide, sodium carbonate, tetramethylammonium hydroxide (TMAH) of the concentration of 0.1 to 10 weight % can be used. If necessary, the developing solution may further include water-soluble organic solvent such as methanol, ethanol, and a surfactant of a proper amount.

Hereinafter, the preferable examples are provided for better understanding of the present invention. However, the present invention is not limited by the following examples.

EXAMPLE 1-1

Preparation of Photosensitive Compound Represented by the Formula 2a 0.01 mol (4.68 g) of methylene-linked para-cresol tetramer and 0.043 mol (4.52 g) of benzyl chloro methyl ether were added into a 250 ml round reaction flask and then 150 ml of toluene was added for dissolving. Thereafter the reflux-reaction was carried out for 6 hours while stirring under the nitrogen atmosphere. The solid component obtained by removing the solvent after completion of the reaction was re-crystallized with 250 ml of tetrahydrofuran(THF) to obtain white-powered compound represented by Formula 2a(Yield: 90%, $^1$H-NMR: s(7.2, 20H), s(6.8, 4H), s(6.5, 6H), s(6.0, 6H), s(4.6, 6H), s(2.4, 12H)).

[Formula 2a]

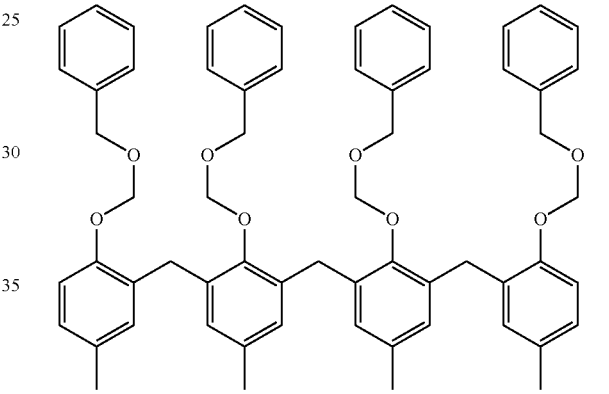

EXAMPLE 1-2

Preparation of Photosensitive Compound Represented by the Formula 2b 0.01 mol (3.06 g) of 1,1,1-tris(4-hydroxyphenyl)ethane and 0.032 mol (3.65 g) of glutaric anhydride were added into a 250 ml round reaction flask and then 150 ml of toluene was added for dissolving. Thereafter the reflux-reaction was carried out for 12 hours while stirring under the nitrogen atmosphere. After the reaction, the solvent was removed and without an additional refining process a white-powered intermediate of compound represented by Formula 2b was obtained(Yield: 70%, $^1$H-NMR: s(7.09, 12H), t(2.23, 12H), s(2.0, 3H), m(1.8, 6H)).

0.01 mol (6.5 g) of the intermediate was added to 500 ml 2-neck round flask and then 250 ml of THF solvent was poured and stirred by a magnetic bar for dissolving. Thereafter, under the dry nitrogen atmosphere, 20 wt % THF solution of 0.032 mol (0.93 g) of methoxymethyl chloride was added, and the reaction was carried out for 12 hours at room temperature. After the completion of the reaction, the solvent was removed under the reduced pressure and 6.63 g of the photosensitive compound represented by the Formula 2b was obtained (Yield: 85%, $^1$H-NMR: s(7.1, 12H), s(6.1, 6H), s(3.2, 9H), t(2.21, 12H), s(2.1, 3H), m(1.7, 6H)).

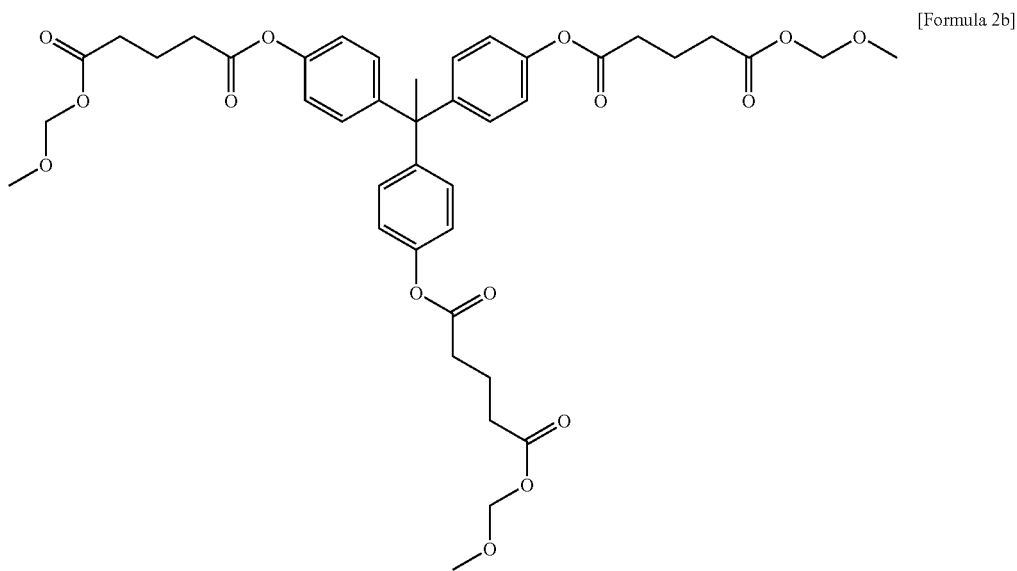

[Formula 2b]

EXAMPLE 1-3

Preparation of Photosensitive Compound Represented by the Formula 2c 0.1 mol (8.4 g) of 3,4-dihydro-2H-pyran and 0.1 mol (13.8 g) of bromoaceticacid were added into a 250 ml round reaction flask and then 150 ml of THF was added to dissolve them. Then 0.6 g of p-toluenesulfonic acid was added as a catalyst while stirring under the nitrogen atmosphere. Thereafter the reflux-reaction was carried out for 12 hours. After the reaction, a liquid intermediate of compound represented by Formula 2c was obtained through a vacuum distillation (Yield: 65%, $^1$H-NMR: t(6.07, 1H), s(4.26, 2H), t(3.6,2H), t(1.84, 2H), m(1.6, 4H)).

0.01 mol (2.9 g) of 4,4',4''-trihydroxytriphenylmethane and 0.032 mol (7.1 g) of the intermediate obtained were added to 250 ml 2-neck round flask and then 80 ml of THF solvent was poured and stirred by a magnetic bar for dissolving. Thereafter, under the dry nitrogen atmosphere, 0.21 g of NaH was added, and the reaction was carried out for 6 hours at room temperature. After the completion of the reaction, the solvent was removed under the reduced pressure to obtain a solid component. The obtained solid component was re-crystallized with 50 ml of ethylacetate solvent to produce 3.9 g of the photosensitive compound represented by the Formula 2c (Yield: 55%, $^1$H-NMR: s(6.9, 6H), s(6.6, 6H), t(6.1, 3H), s(5.4, 1H), s(4.9, 6H), t(3.6, 6H), t(1.84, 6H), m(1.6, 12H)).

[Formula 2c]

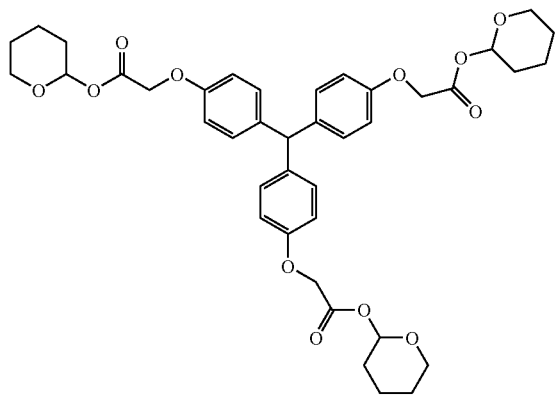

EXAMPLE 1-4

Preparation of Photosensitive Compound Represented by the Formula 2d 0.01 mol (6.5 g) of the intermediate of the compound represented by Formula 2b, obtained from a reaction of 1,1,1-tris(4-hydroxyphenyl)ethane and glutaric anhydride, was dissolved with 120 ml of dried-THF solvent. Then 0.032 mol (3.8 g) of thionyl chloride was dropped for 30 minutes to make a reaction solution. The reaction solution was stirred under the nitrogen atmosphere for 12 hours and then distilled under the reduced pressure to obtain 1,1,1-tris(4-(4'-chlorocarbonylbutanoate-oxy)phenyl)ethane. Without a refining process, the obtained 1,1,1-tris(4-(4'-chlorocarbonylbutanoate-oxy)phenyl)ethane was dissolved with 100 ml of dried-THF solvent, and 0.032 mol (5.3 g) of 2-methyl-2-adamantanole and 0.032 mol (3.2 g) of triethylamine were added. Then the reflux reaction was carried out for 12 hours. Next, the solid component obtained by the distillation under the reduced pressure was re-crystallized with 50 ml of ethylacetate to obtain 4.6 g of compound represented by Formula 2d (Yield:42%, $^1$H-NMR: s(7.1, 12H), s(2.5, 3H), t(2.2, 12H), m(2.0, 12H), m(1.5, 45H)).

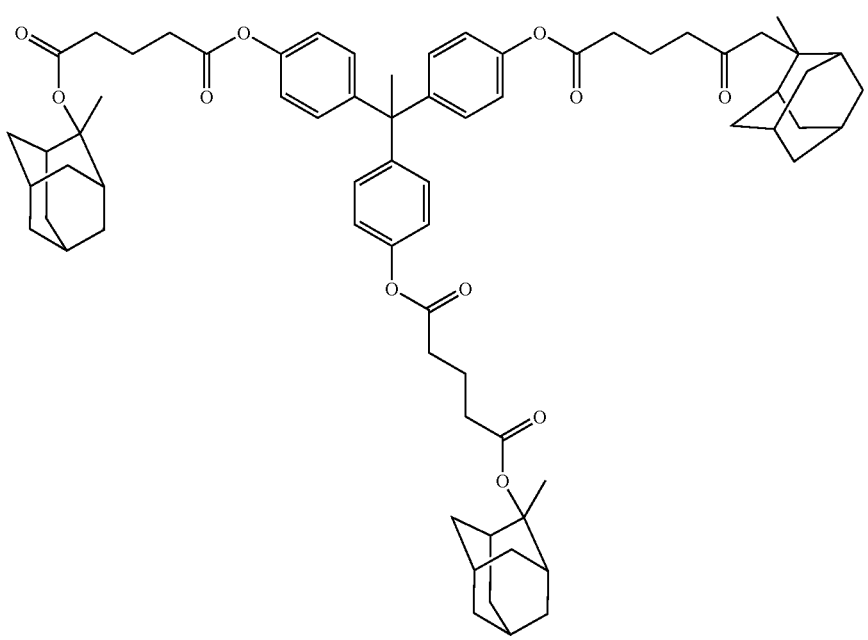

[Formula 2d]

EXAMPLE 1-5

Preparation of Photosensitive Compound Represented by the Formula 2e 0.03 mol (5.0 g) of 2-methyl-2-adamantanole and 0.032 mol (3.2 g) of triethylamine were added to 250 ml round flask, and 80 ml of THF was added to dissolve them (to make THF solution). Then 0.03 mol (0.78 g) of chloro acetyl chloride was dropped to 20 ml of THF solution for 30 minutes. The reaction was carried out for 12 hours under the nitrogen atmosphere while stirring The reactant was distilled under the reduced pressure to obtain a product. The product was refined by re-crystallizing with 50 ml of ethylacetate to obtain an intermediate, 2-methyl-2-adamantyl-chloroacetate (Yield: 50%, $^1$H-NMR: s(4.3,2H), m(2.5, 1H), m(2.0,2H), m(1.5, 10H), m(1.1, 4H)).

0.01 mol (3.1 g) of 1,1,1-tris(4-hydroxyphenyl)ethane and 0.032 mol (7.7 g) of the intermediate synthesized above were added to 250 ml 2-neck round flask and then dissolved with 80 ml of THF solvent while being stirred with a magnetic bar. Then, 0.21 g of NaH was added under the dry nitrogen atmosphere and the reaction was carried out for 6 hours at room temperature. After the completion of the reaction, the solvent was removed by a distiller under the reduced pressure to obtain a solid component. The solid component was re-crystallized with 50 ml of ethylacetate solvent to obtain 3.2 g of a compound represented by Formula 2e(Yield: 35%, $^1$H-NMR: s(6.8, 12H), s(4.9, 6H), m(2.5, 3H), s(2.0, 3H) m(1.6, 48H)).

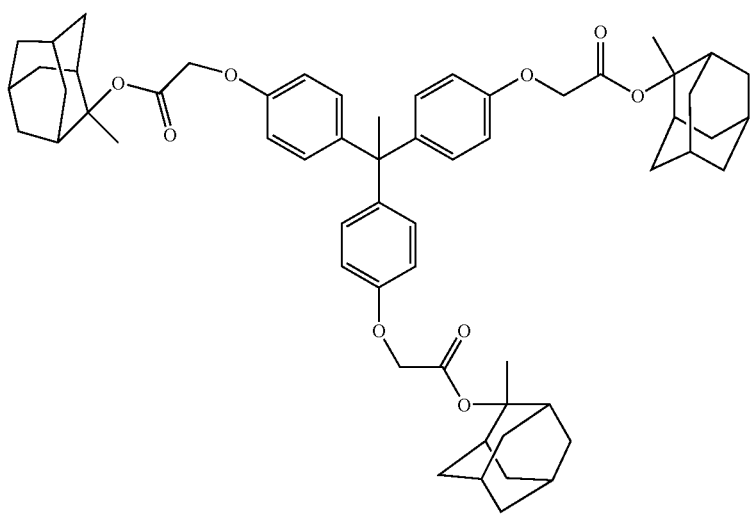

[Formula 2e]

EXAMPLE 1-6

Preparation of Photosensitive Compound Represented by the Formula 2f

Except for using 0.01 mol (4.68 g) of methylene-linked para-cresol tetramer instead of 0.01 mol (3.1 g) of 1,1,1-tris(4-hydroxyphenyl)ethane, 3.5 g of the photosensitive compound represented by the Formula 2f was obtained according to the same manner of Example 1-5 (Yield: 27%, ¹H-NMR: s(6.7, 10H), s(4.9, 8H), m(2.5, 4H), s(2.4, 12H), m(1.6, 64H)).

[Formula 2f]

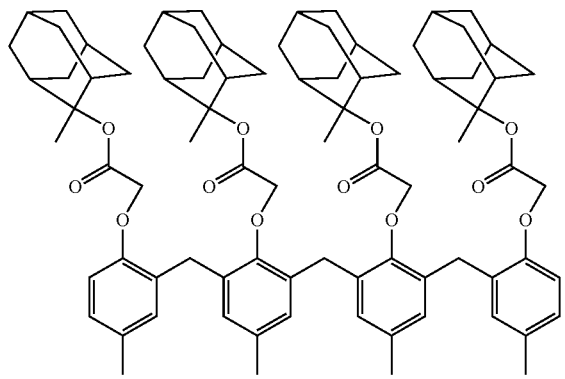

EXAMPLE 1-7

Preparation of Photosensitive Compound Represented by the Formula 2g

Except for using 0.01 mol (7.08 g) of methylene-linked phenol-derivative hexamer instead of 0.01 mol (3.1 g) of 1,1,1-tris(4-hydroxyphenyl)ethane, 3.9 g of the photosensitive compound represented by the Formula 2 g was obtained according to the same manner of Example 1-5 (Yield: 20%, ¹H-NMR: s(6.6, 14H), s(5.3, 2H), s(4.9, 12H), m(2.S, 6H), s(2.4, 18H), m(1.6, 96H)).

EXAMPLE 1-8

Preparation of Photosensitive Compound Represented by the Formula 2h

Except for using 0.01 mol (3.45 g) of methylene-linked para-cresol trimer instead of 0.01 mol (3.1 g) of 1,1,1-tris(4-hydroxyphenyl)ethane, 5.4 g of the photosensitive compound represented by the Formula 2h was obtained according to the same manner of Example 1-5 (Yield: 55.9%, ¹H-NMR:s(6.7, 8H), s(4.9, 6H), s(3.8, 4H), m(2.48, 3H), s(2.35, 3H), m(1.6, 48H)).

[Formula 2h]

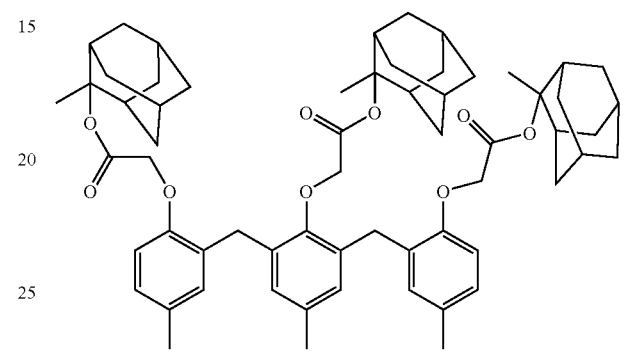

EXAMPLES 2-1 to 2-8

Preparation of Photoresist Composition and Formation of Photoresist Pattern Using the Photoresist Composition The photosensitive compound in the following Table 1, 400 weight parts of PGMEA as an organic solvent with

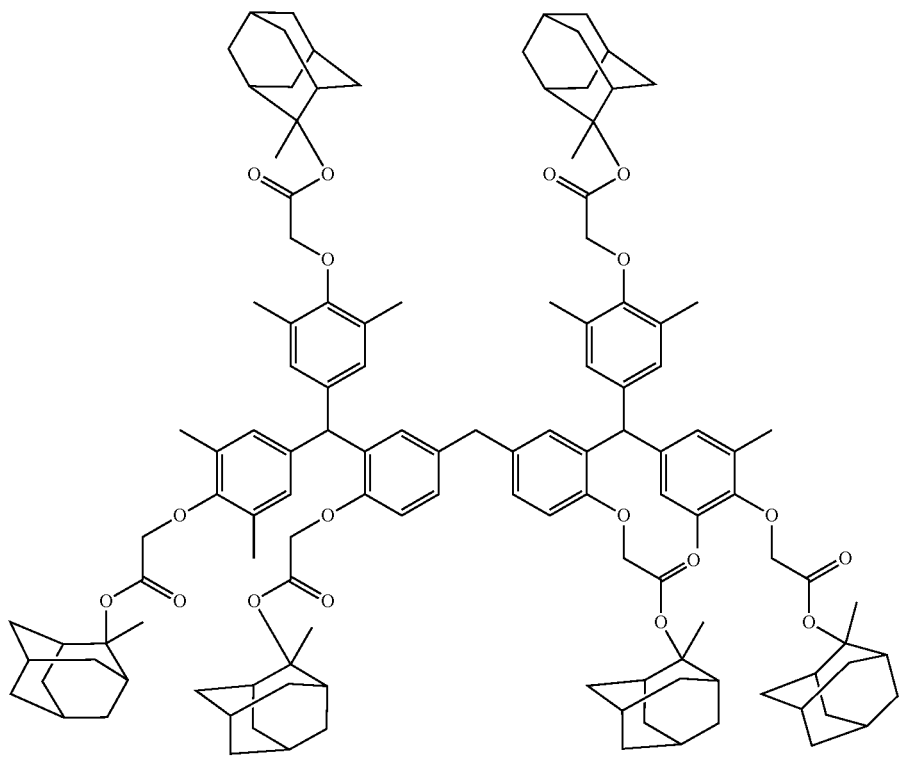

respect to 100 weight parts of the photosensitive compound in Table 1, 4.5 weight parts of triphenylsulfonium nonaflate as a PAG with respect to 100 weight parts of the photosensitive compound in Table 1 and 2 weight parts of trioctylamine as a resist quencher with respect to 100 weight parts of the photosensitive compound in Table 1 were mixed. The mixture was stirred for 4 hours at room temperature and filtrated to manufacture a photoresist composition.

TABLE 1

| | Photosensitive compound |
|---|---|
| Example 2-1 | The compound of Formula 2a, 25 g |
| Example 2-2 | The compound of Formula 2b, 25 g |
| Example 2-3 | The compound of Formula 2c, 25 g |
| Example 2-4 | The compound of Formula 2d, 25 g |
| Example 2-5 | The compound of Formula 2e, 25 g |
| Example 2-6 | The compound of Formula 2f, 25 g |
| Example 2-7 | The compound of Formula 2g, 25 g |
| Example 2-8 | The compound of Formula 2h, 25 g |

The photoresist composition manufactured was spin-coated by 1000 Å on a silicon wafer to form a photoresist thin film. Then the photoresist thin film was soft-baked in an oven or heat fan at 130° C. for 90 seconds and then exposed by EUVL (extreme ultraviolet lithography) instrument. Thereafter, the photoresist thin film was again baked at 130° C. for 90 seconds. The baked wafer was dipped in 2.38 wt % TMAH (trimethyl ammonium hydroxide) aqueous solution for 40 seconds for developing to form 32 nm L/S (line/space) pattern. The features of the formed photoresist pattern were measured and the results are shown in the following Table 2. The electron microphotograph of the photoresist pattern according to Example 1 is shown in FIG. 1.

TABLE 2

| | Resolution | LER | Coating uniformity | Etching resistance to novolac resin | Scum control | Profile |
|---|---|---|---|---|---|---|
| Example 2-1 | <32 nm | 1.1 nm | 2.1% | 100% | Free | Rectangular |
| Example 2-2 | <32 nm | 1.7 nm | 2.5% | 95% | Free | Rectangular |
| Example 2-3 | <32 nm | 1.6 nm | 1.9% | 97% | Free | Rectangular |
| Example 2-4 | <32 nm | 1.9 nm | 2.9% | 95% | Free | Rectangular |
| Example 2-5 | <32 nm | 1.5 nm | 2.0% | 98% | Free | Rectangular |
| Example 2-6 | <32 nm | 1.8 nm | 3.0% | 100% | Free | Rectangular |
| Example 2-7 | <32 nm | 1.7 nm | 2.4% | 100% | Free | Rectangular |
| Example 2-8 | <32 nm | 1.5 nm | 2.9% | 98% | Free | Rectangular |

In Table 2, the coating uniformity was measured by Nanospec instrument, and the etching resistance is the thickness variation after a dry etching and was measured by Nanospec instrument. Scum and profile were observed by a naked eye. From Table 2, the photosensitive compound and the photoresist composition including the same of the present invention enable the minimum and uniform pattern formation so that the resolution of the lithography process of less than 32 nm can be made and also line edge roughness (LER) of less than 3 nm (3 sigma) can be controlled. Also, the photoresist composition of the present invention has advantages of excellent coating uniformity in that non-uniformity of the coating film is less than 3%, dry etching resistance which is as good as novolac resin, and low scum generation.

The invention claimed is:

1. A photosensitive compound having a structure selected from a group consisting of the following Formula 1a and Formula 1b,

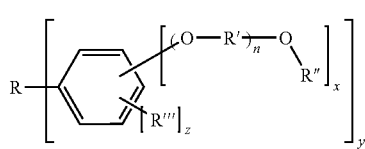

wherein, n is 0 or 1, x is 1, 2, 3, 4 or 5, y is 2, 3, 4, 5 or 6, z is 0, 1, 2, 3 or 4, R, R' and R" are independently hydrocarbon group of 1 to 30 carbon atoms, and R''' is a hydrogen atom or hydrocarbon group of 1 to 30 carbon atoms;

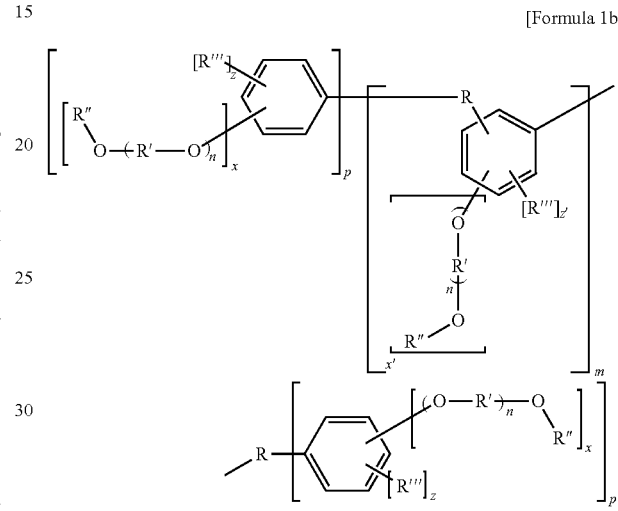

wherein, n, x, z, R, R' R" and R''' are the same defined as in Formula 1a, x' is 1, 2, 3 or 4, z' is 0, 1, 2 or 3, and p and m are independently 1 or 2, wherein in Formula 1a and Formula 1b: i) carbonyl(C=O) groups or carboxyl(—COO—) groups are positioned at the both ends of the R; or ii) n =1 and carbonyl(C=O) groups or carboxyl(—COO—) groups are positioned at the both ends of R'.

2. The photosensitive compound of claim 1, wherein R, R', R" and R''' each is a chain type and/or a ring type of aliphatic and/or aromatic hydrocarbon group.

3. The photosensitive compound of claim 1, wherein the R" include an ether compound structure or an ester compound structure which includes oxygen(O) atom.

4. The photosensitive compound of claim 1, wherein the photosensitive compound is selected from a group consisting of compounds represented by the following Formulas 2b and 2d,

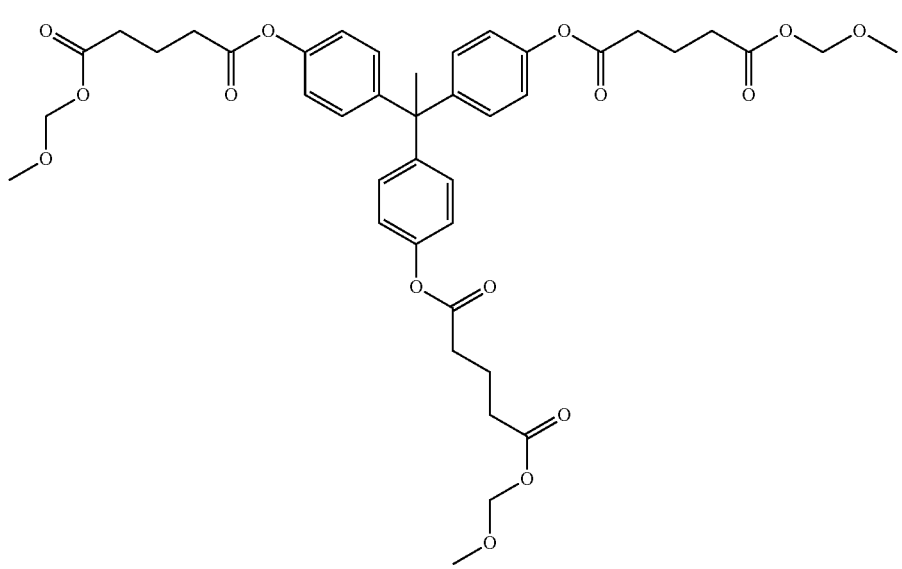

[Formula 2b]

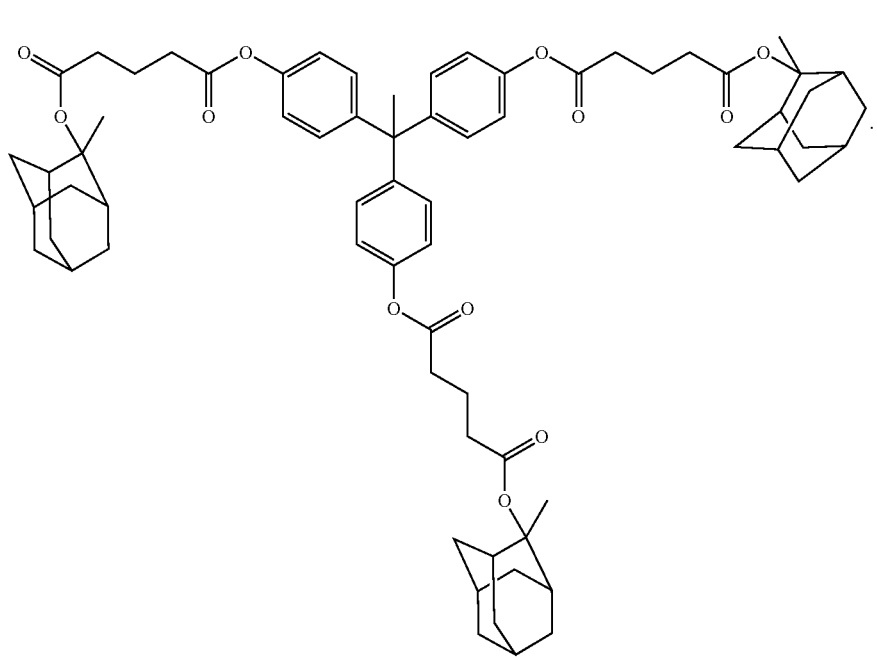

[Formula 2d]

5. A photoresist composition comprising:
(a) 1 to 85 weight % of a photosensitive compound having a structure selected from a group consisting of the following Formula 1a and Formula 1b,

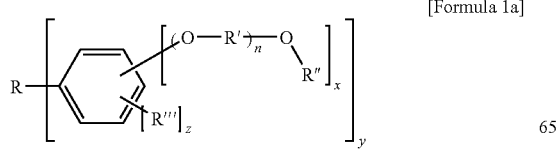

[Formula 1a]

wherein, n is 0 or 1, x is 1, 2, 3, 4 or 5, y is 2, 3, 4, 5 or 6, z is 0, 1, 2, 3 or 4, R, R' and R'' are independently hydrocarbon group of 1 to 30 carbon atoms, and R''' is a hydrogen atom or hydrocarbon group of 1 to 30 carbon atoms;

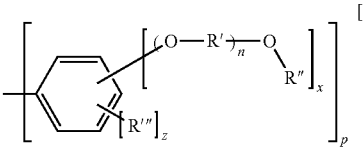

[Formula 1a]

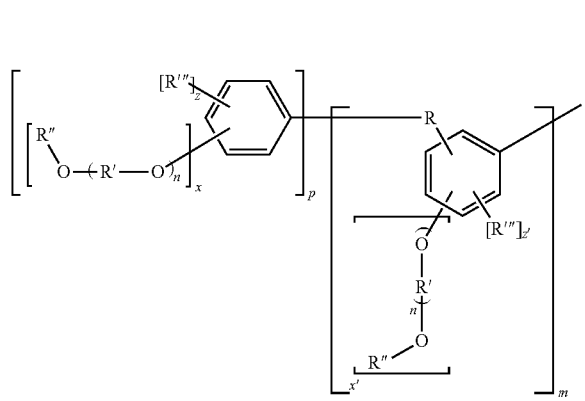

wherein, n, x, z, R, R' R'" and R'" are the same defined as in Formula 1a, x' is 1, 2, 3 or 4, z' is 0, 1, 2 or 3, and p and m are independently 1 or 2;
(b) 0.05 to 15 weight parts of a photo-acid generator with respect to 100 weight parts of the photosensitive compound; and
(c) 10 to 5000 weight parts of an organic solvent with respect to 100 weight parts of the photosensitive compound,
wherein in Formula 1a and Formula 1b: i) carbonyl(C=O) groups or carboxyl(—COO—) groups are positioned at the both ends of the R; or ii) n =1 and carbonyl(C=O) groups or carboxyl(—COO—) groups are positioned at the both ends of R'.

6. The photoresist composition of claim 5, further comprising 0.01 to 10 weight parts of a base compound with respect to 100 weight parts of the photosensitive compound, wherein, ture selected from a group consisting of the following Formula 1a and Formula 1b,

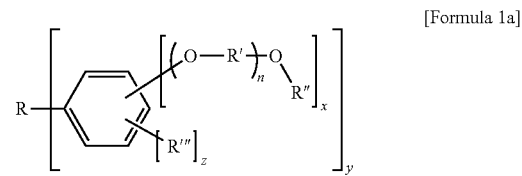

[Formula 1a]

wherein, n is 0 or 1, x is 1, 2, 3, 4 or 5, y is 2, 3, 4, 5 or 6, z is 0, 1, 2, 3 or 4, R, R' and R" are independently hydrocarbon group of 1 to 30 carbon atoms, and R'" is a hydrogen atom or hydrocarbon group of 1 to 30 carbon atoms;

[Formula 1b]

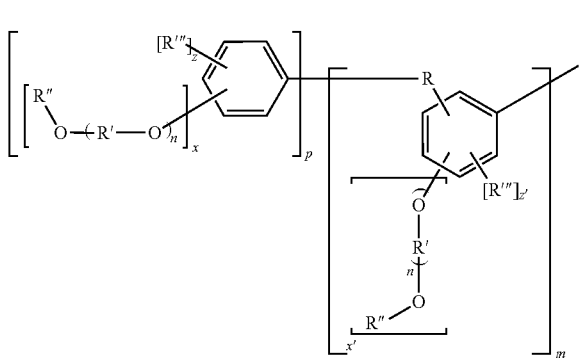

the base compound is selected from a group of consisting of tri-ethylamine, tri-iso-butylamine, tri-iso-octylamine, di-ethanolamine, tri-ethanolamine and mixture thereof.

7. A method for forming a photoresist pattern, comprising the step of:
a) coating a photoresist composition on a substrate to form a photoresist layer;
b) exposing the photoresist layer to a light;
c) heating the exposed photoresist layer; and
d) developing the heated photoresist layer to form the photoresist pattern,
wherein the photoresist composition comprises i) 1 to 85 weight % of a photosensitive compound having a strucwherein, n, x, z, R, R' R" and R'" are the same defined as in Formula 1a, x' is 1, 2, 3 or 4, z' is 0, 1, 2 or 3, and p and m are independently 1 or 2;
(ii) 0.05 to 15 weight parts of a photo-acid generator with respect to 100 weight parts of the photosensitive compound; and
(iii) 10 to 5000 weight parts of an organic solvent with respect to 100 weight parts of the photosensitive compound,
wherein in Formula 1a and Formula 1b: i) carbonyl(C=O) groups or carboxyl(—COO—) groups are positioned at the both ends of the R; or ii) n=1 and carbonyl(C=O) groups or carboxyl(—COO—) groups are positioned at the both ends of R'.

* * * * *